United States Patent
Dickie et al.

(10) Patent No.: US 12,419,613 B2
(45) Date of Patent: Sep. 23, 2025

(54) SYSTEMS AND METHODS FOR AUTOMATED BLADDER MEASUREMENT

(71) Applicant: Clarius Mobile Health Corp., Vancouver (CA)

(72) Inventors: Kris Dickie, Vancouver (CA); Nishant Uniyal, Vancouver (CA); Benjamin Eric Kerby, Richmond (CA); Matt Potma, Vancouver (CA); Wasiu Raimi, Ottawa (CA)

(73) Assignee: Clarius Mobile Health Corp., Vancouver (CA)

( * ) Notice: Subject to any disclaimer, the term of this patent is extended or adjusted under 35 U.S.C. 154(b) by 61 days.

(21) Appl. No.: 18/407,290

(22) Filed: Jan. 8, 2024

(65) Prior Publication Data
US 2025/0221691 A1   Jul. 10, 2025

(51) Int. Cl.
 *A61B 8/00* (2006.01)
 *A61B 8/08* (2006.01)
 *G06T 7/62* (2017.01)

(52) U.S. Cl.
 CPC .......... *A61B 8/5223* (2013.01); *A61B 8/085* (2013.01); *G06T 7/62* (2017.01);
 (Continued)

(58) Field of Classification Search
 CPC ......... A61B 8/5223; A61B 8/085; G06T 7/62; G06T 2207/10132; G06T 2207/20081; G06T 2207/30004
 See application file for complete search history.

(56) References Cited

U.S. PATENT DOCUMENTS

| | | |
|---|---|---|
| 6,406,431 B1 | 6/2002 | Barnard et al. |
| 9,763,615 B2 | 9/2017 | Xu |

(Continued)

FOREIGN PATENT DOCUMENTS

| | | |
|---|---|---|
| EP | 1551305 B1 | 12/2015 |
| EP | 2186483 B1 | 6/2020 |

*Primary Examiner* — Chao Sheng
(74) *Attorney, Agent, or Firm* — Julian Ho; Susan Ben-Oliel

(57) ABSTRACT

A method for automatically measuring a bladder on an ultrasound image feed, acquired from an ultrasound scanner comprises displaying, on a screen that is communicatively connected to the ultrasound scanner, the ultrasound image feed comprising ultrasound image frames of a bladder; deploying an AI model to execute on a computing device communicably connected to the ultrasound scanner, wherein the AI model is trained so that when the AI model is deployed, the computing device identifies and predicts a view of the bladder, from one of a sagittal view and a transverse view; acquiring, at the computing device, a new ultrasound image during ultrasound scanning; processing, using the AI model, the new ultrasound image to identify and predict the view of the bladder, wherein the prediction is an AI model output; wherein if f the AI model output predicts that the new ultrasound image comprises a sagittal view of the bladder, automatically applying one caliper set along a superior-inferior dimension of the bladder and measuring the superior-inferior dimension; and wherein if the AI model output predicts that the new ultrasound image comprises a transverse view of the bladder, applying two caliper sets along each of a length and a width of the bladder and measuring the length and width thereof.

19 Claims, 16 Drawing Sheets

(52) U.S. Cl.
CPC ............... *G06T 2207/10132* (2013.01); *G06T 2207/20081* (2013.01); *G06T 2207/30004* (2013.01)

(56) References Cited

U.S. PATENT DOCUMENTS

| | | | |
|---|---|---|---|
| 2012/0053467 A1* | 3/2012 | Betts .................. | G16H 50/30 600/449 |
| 2016/0192904 A1 | 7/2016 | Kim et al. | |
| 2017/0124700 A1* | 5/2017 | Sarojam ................. | A61B 8/523 |
| 2020/0196979 A1 | 6/2020 | Van Heesch et al. | |

* cited by examiner

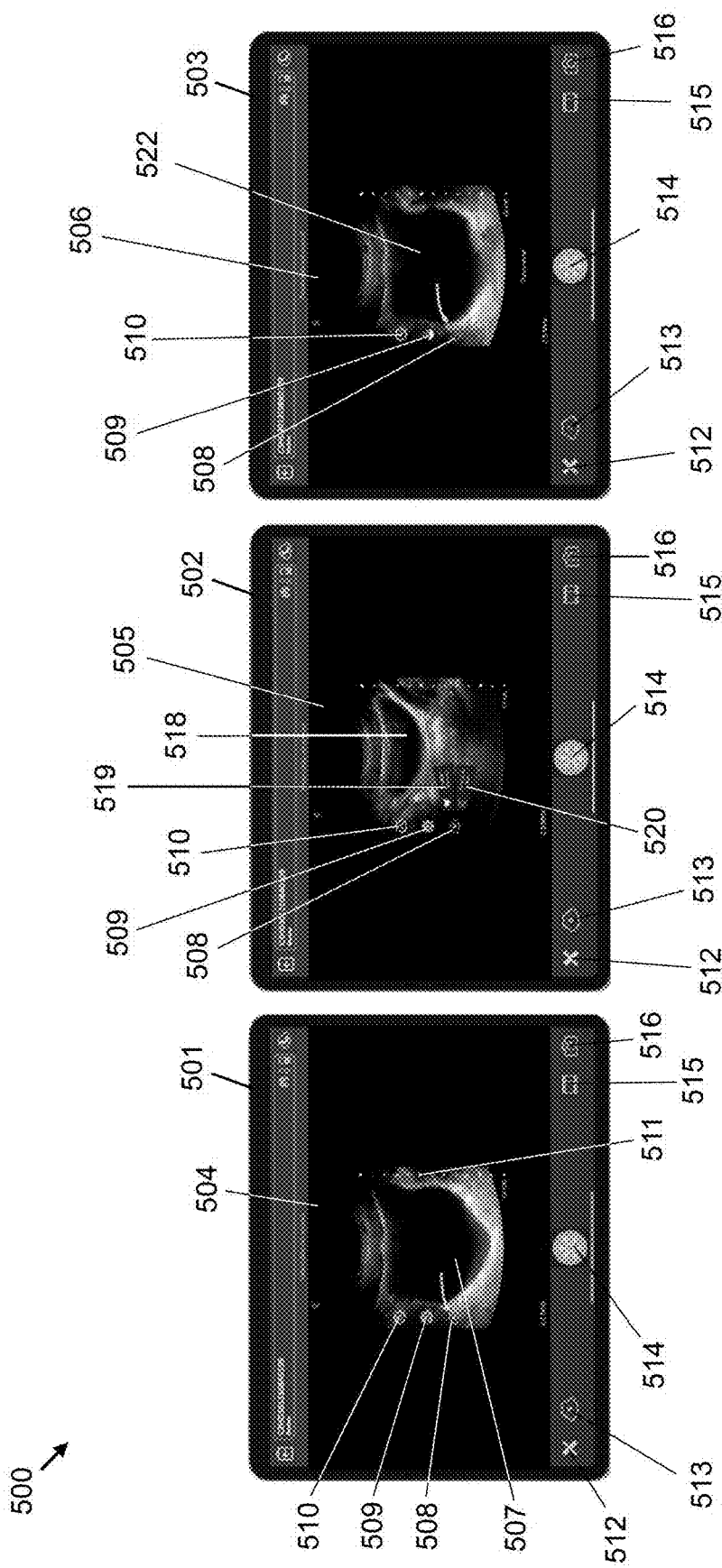

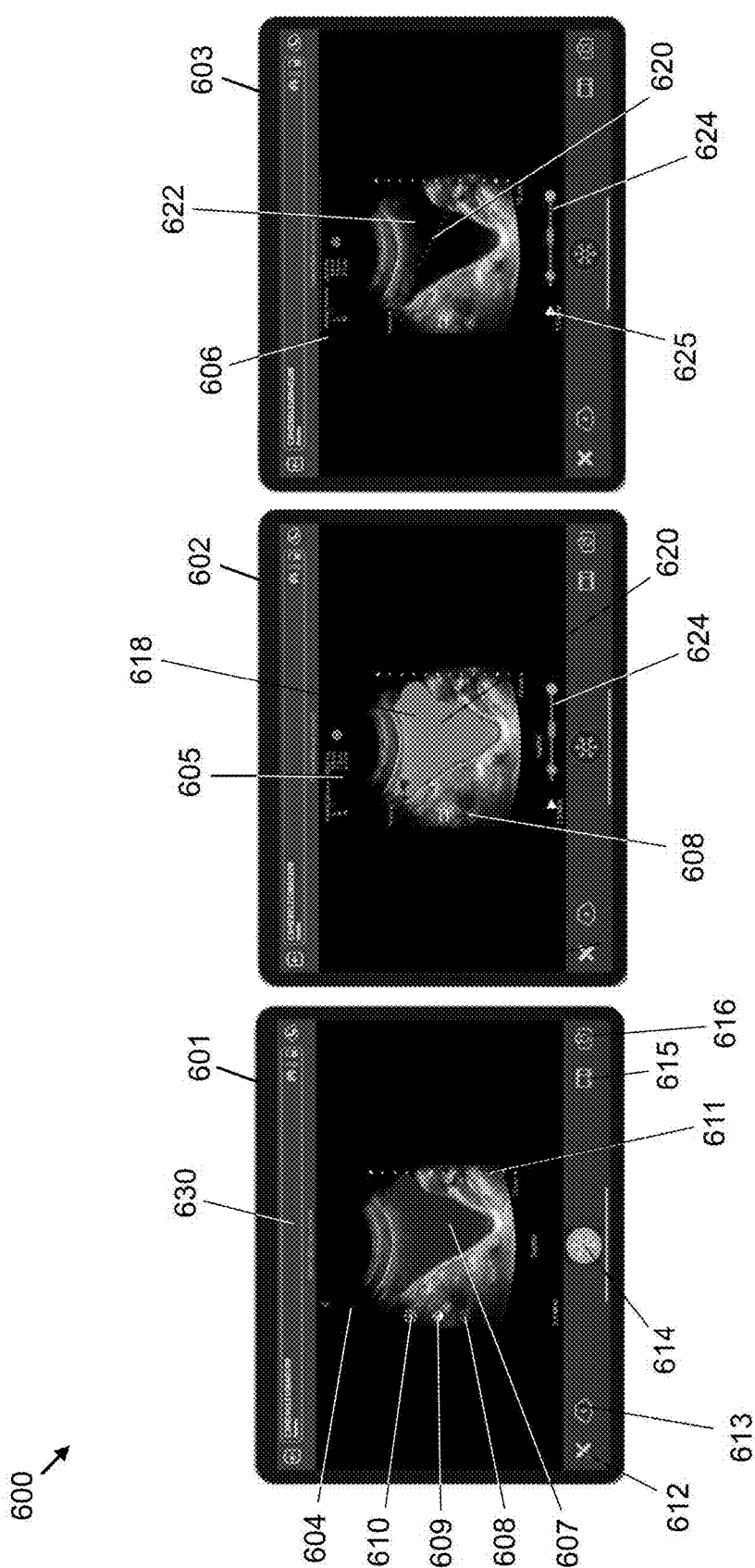

SYSTEMS AND METHODS FOR AUTOMATED BLADDER MEASUREMENT

FIELD OF THE INVENTION

The present disclosure relates generally to ultrasound imaging, and in particular, systems and methods for determining bladder volume during ultrasound imaging.

BACKGROUND OF THE INVENTION

It is well known that bladder dysfunction is associated with many clinical situations that require treatment. In many of these cases, it is important to accurately determine the bladder volume. Under other circumstances, such as post-surgical recovery, where there is a temporary loss of bladder sensation and/or loss of normal urination mechanisms, excessive swelling of the bladder must be avoided. Under these circumstances, urination is performed by introducing a catheter. However, the significant disadvantages of unnecessary catheterization range from an unpleasant situation for the patient to the possibility of a serious infection. In addition, urinary catheters have long been associated with higher UTI rates, longer hospital stays, and increased costs.

It is desirable for clinicians to be able to rapidly and reliably measure bladder volume with consistent accuracy. One tool used to measure bladder volume is an ultrasound scanner. Ultrasound diagnostics are well known today by imaging real-time cross sections of human organs. In order to image a cross section, the acoustic beam must be scanned electronically or mechanically through the cross section to be imaged. The volume is often calculated based on the bladder outline obtained in two orthogonal planes with the geometric assumption of the bladder shape. For three-dimensional or volumetric sonography, a sound beam must be scanned throughout the organ. It is thus necessary that a user/operator scan in both sagittal and transverse planes in order to determine height, width and length measurements. Depth and width are measured by the placement of two sets of calipers on the transverse view and height is measured by the placement of one set of calipers on the sagittal view. Generally, an ultrasound operator must determine the specific view which is imaged in order for the measurements to be taken and subsequently the operator places the correct number of calipers to by manipulation on user interface screen. There are drawbacks to this traditional operator placement method.

Modern, portable ultrasound medical imaging systems (POCUS or point of care ultrasound systems) connect to off-the-shelf display computing devices such as those running iOS™ or Android™ operating systems. As compared to traditional cart-based and dedicated ultrasound systems that have keyboards, a trackball or other physical input controls, off-the-shelf display computing devices, such as for example, iPADS and iPhones typically receive input from users via touchscreens. While the use of these touchscreen inputs may allow for a more familiar user interface, it may be difficult to be as precise using touchscreen input versus the physical controls of traditional ultrasound systems.

One area where this lack of precision may present a challenge is performing measurements on ultrasound images such as those required to place calipers for bladder measurements. Traditional manual approaches to caliper placement involve placing a first edge of the caliper on one side of the imaged structure to be measured, and then placing the second edge of the caliper on an opposing side of the imaged structure to be measured. Using a touchscreen to precisely place the edges of the calipers may be difficult since a fingertip of an ultrasound operator may typically be larger than that of the arrowhead of a cursor manipulated by manual controls (e.g., a trackball). These challenges may be even more pronounced in instances where the ultrasound operator is wearing protective gloves as they have less tactile feedback about finger placement.

Additionally, the screen size of off-the-shelf display computing devices vary greatly. In certain instances, measurements may be performed on tablet-sized computing devices with larger displays, and distances between points for caliper placement may be easily positioned. However, in certain other instances, the off-the-shelf display computing devices may also be smartphones with smaller display sizes. In these instances, a fingertip may have less pinpoint accuracy and it may be difficult to perform a measurement if the distance that is desired to be measured is small. For example, it may be difficult to place the two edges of a caliper on an ultrasound image because the two points are displayed close together on a smaller display.

Some traditional attempts at addressing these challenges include using measurement tools to automatically place calipers. However, these automatic tools rely on image analysis techniques that may not be accurate, and thus, may result in incorrect caliper placements. For example, some of these image analysis tools include contour identification techniques (e.g., an active contour model or "snakes" algorithm) that attempt to identify a structure within an ultrasound image. However, these algorithms typically require complex mathematical operations such as solving of differential equations that are computationally intensive. This may make them difficult to perform on mobile devices that have limited processing capabilities and battery power.

These and other drawbacks further increase the complexity and inaccuracy of bladder measurement. There is thus a need for improved ultrasound systems and methods for performing a measurement of an ultrasound image displayed on a touchscreen device and, in particular, for performing measurements of the depth, height and width of a bladder in an ultrasound image. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which:

FIG. 5A is an image of a screen/display interface showing a step to initiate a bladder preset, in accordance with at least one embodiment of the present invention;

FIG. 5B is an image of a screen/display interface showing a next step (subsequent to FIG. 5A), to select a bladder volume preset, in accordance with at least one embodiment of the present invention;

FIG. 5C is an image of a screen/display interface showing a step to initiate deployment of the AI model for the bladder measurement preset in accordance with at least one embodiment of the present invention;

FIG. 6A is an image showing the result of performing acts of the present methods on an example ultrasound image, in accordance with at least one embodiment of the present invention;

FIG. 6B is an image showing the result of performing acts of the present methods on an example ultrasound image, in accordance with at least one embodiment of the present invention;

FIG. 6C is an image showing the result of performing acts of the present methods on an example ultrasound image, in accordance with at least one embodiment of the present invention;

Figure 1:
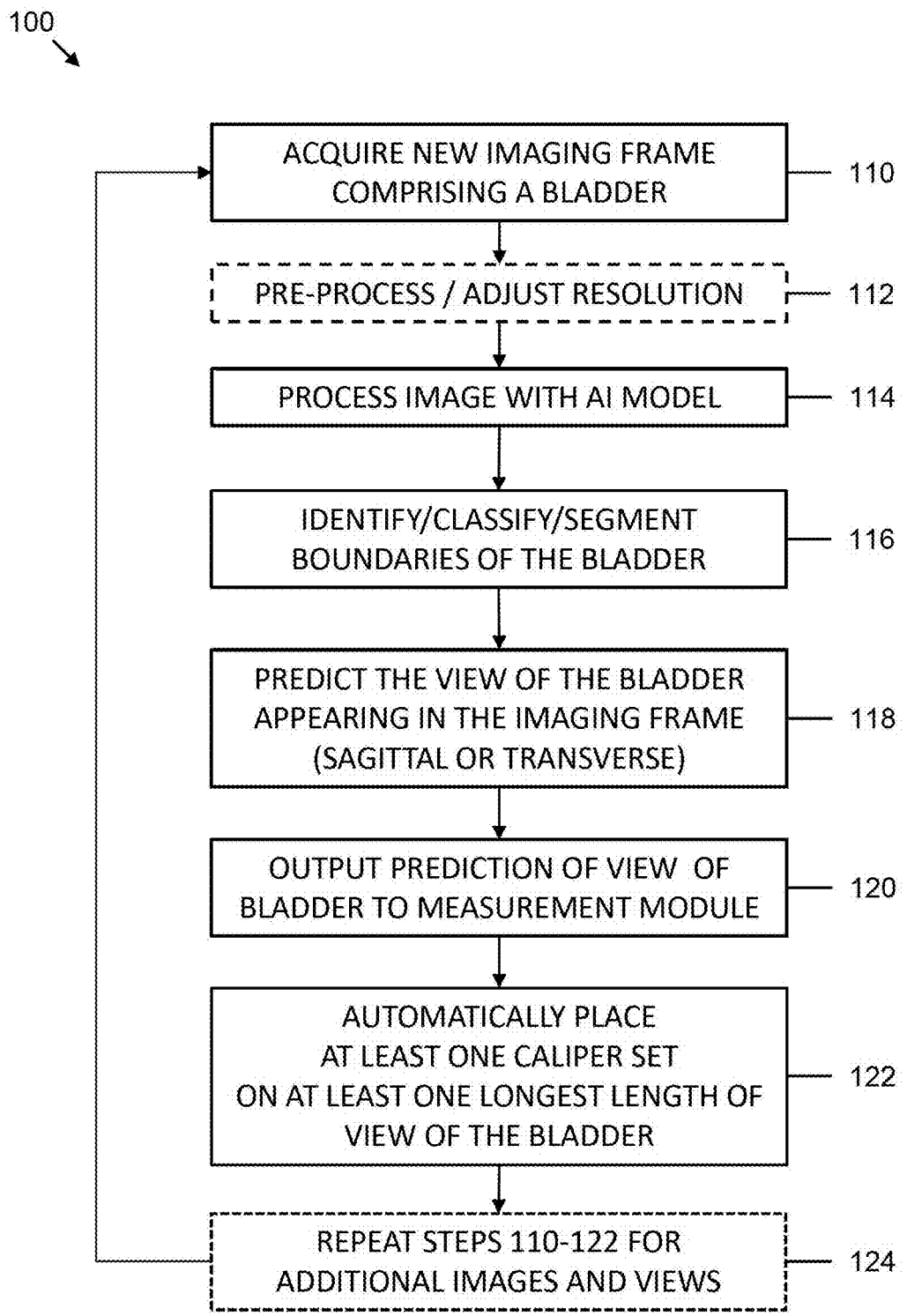
FIG. 1 is a flowchart diagram showing steps of a method of automatically performing caliper placement on an AI model predicted view of a bladder, on an ultrasound image displayed on a device, in accordance with at least one embodiment of the present invention.

Unless otherwise specifically noted, articles depicted in the drawings are not necessarily drawn to scale.

DETAILED DESCRIPTION OF THE INVENTION

A. Glossary

The term "AI model" means a mathematical or statistical model that may be generated through artificial intelligence techniques such as machine learning and/or deep learning. For example, these techniques may involve inputting labeled or classified data into a neural network (e.g., a deep neural network) algorithm for training, so as to generate a model that can make predictions or decisions on new data without being explicitly programmed to do so. Different software tools (e.g., TensorFlow™, PyTorch™, Keras™) may be used to perform machine learning processes. Within the scope of the invention, an AI model is trained to identify and predict a view of a bladder, from one a transverse view of a bladder and a sagittal view of a bladder, such identification employing, for example, a segmented mask of the bladder (for example, using one of a plurality of edge detection techniques) or a classifier model. It is to be understood that the present invention is not to be limited to any one means of deploying the AI model for such detection.

The term "caliper set" and "calipers" (whether singular or plural) refers generally to a pair of digital measuring lines, i.e. connected point to point, (viewable on a display screen, on an ultrasound image) and used to determine one or more cross-sectional dimensions of a bladder on that ultrasound image. Within an embodiment of the present invention, measurements are taken and saved in a workflow associated with an application (for example, the Clarius App) when on a live imaging screen after an ultrasound image has been frozen, as well as on a captured ultrasound image prior to an examination being completed. Measurements may be performed by automatic placement of one or more calipers on the display screen, based upon an AI predicted view of the bladder. A full set of measurements is acquired once all calipers are placed across both a sagittal (longitudinal) view and transverse view. Generally, a center of the crosshairs of the caliper correlate to the ultrasound pixel that is focused on for making an exact measurement.

The term "communications network" and "network" can include both a mobile network and data network without limiting the term's meaning, and includes the use of wireless (e.g. 2G, 3G, 4G, 5G, WiFi®, WiMAX®, Wireless USB (Universal Serial Bus), Zigbee®, Bluetooth® and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "labeling" refers to an act of labeling either a piece of training data or non-training data. For example, a user may mark a feature on an ultrasound image and identify the anatomy to which the feature corresponds. The result is a labeled piece of data, such as a labeled ultrasound image. Alternatively, and by way of example, an AI model may automatically and without user intervention label one or more segmented features, within an ultrasound image.

The term "module" can refer to any component in this invention and to any or all of the features of the invention without limitation. A module may be a software, firmware or hardware module (or part thereof), and may be located or operated within, for example, in the ultrasound scanner, a display device or a server.

The term "multi-purpose electronic device" or "display device" or "computing "device" or "off-the-shelf display computing device" is intended to have broad meaning and includes devices with a processor communicatively operable with a screen interface, for example, such as, laptop computer, a tablet computer, a desktop computer, a smart phone, a smart watch, spectacles with a built-in display, a television, a bespoke display or any other display device that is capable of being communicably connected to an ultrasound scanner. Such a device may be communicatively operable with an ultrasound scanner and/or a cloud-based server (for example via one or more communications networks).

The term "operator" (or "user") may (without limitation) refer to the person that is operating an ultrasound scanner (for example, a clinician, medical personnel, a sonographer trainer, a student, a vet, a sonographer/ultrasonographer and/or ultrasound technician). This list is non-exhaustive.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for predicting a view of a bladder on an ultrasound image and placing the correct number of calipers in accordance with such a predicted view. In various embodiments, the system may include an ultrasound scanner and a multi-purpose electronic device/display device; and/or an ultrasound scanner, multi-purpose electronic device/display device and a server. The system may include one or more applications operating on a multi-purpose electronic device/display device to which the ultrasound scanner is communicatively connected.

The term "ultrasound image frame" (or "image frame" or "ultrasound frame") refers to a frame of either pre-scan data or post-scan conversion data that is suitable for rendering an ultrasound image on a screen or other display device.

The term "ultrasound transducer" (or "probe" or "ultrasound probe" or "transducer" or "ultrasound scanner" or "scanner") refers to a wide variety of transducer types including but not limited to linear transducer, curved transducers, curvilinear transducers, convex transducers, microconvex transducers, and endocavity probes. In operation, an ultrasound scanner is often communicatively connected to a multi-purpose electronic device/display device to direct operations of the ultrasound scanner, optionally through one or more applications on the multi-purpose electronic device/display device (for example, via the Clarius™ App).

The term "workflow application" or "application" (for example, via the Clarius™ App) or "workflow" refers to a software tool that automates the tasks involved in the bladder measuring process including, but not limited to the following method steps: i) receiving one or more outputs of the trained AI model of the present invention, comprising at least a prediction of view of the bladder on an ultrasound image and then placing one caliper set or two caliper sets along the longest boundary or boundaries of the bladder in the identified view, based at least in part by the prediction of the AI as to the particular view of the bladder imaged in an imaging frame; ii) measuring the width and depth in the transverse view and measuring the superior-inferior dimension (height) in the longitudinal view; and iii) calculating the volume of the bladder using the width, depth and height measurements. In some embodiments of the invention, the workflow application guides the entire process automatically, issuing screen display notifications to users/operators as needed, with triggers to complete tasks or with specific commands, for example, after successfully processing one view of the bladder, to turn the probe either 90 degrees counterclockwise or 90 degrees clockwise to acquire another view of the bladder. In some aspects of the invention, bladder volume measurements only require that the workflow tool be activated once, where the workflow enables: i) activation of an AI model to identify and predict a view of a bladder on an acquired and frozen ultrasound image; and ii) automatic placement of the correct number of caliper sets, based upon the AI model predicted view of the bladder; and iii) capture of measurements from the caliper set(s).

B. Exemplary Embodiments

In a first broad aspect of the present disclosure, there are provided ultrasound systems, ultrasound-based methods, tools and workflows for predicting a view of a bladder on an ultrasound image and then automatically placing the correct number of calipers, in accordance with such the predicted view.

In another aspect of the present disclosure, there is provided a method for automatically measuring a bladder on an ultrasound image feed, acquired from an ultrasound scanner comprising displaying, on a screen that is communicatively connected to the ultrasound scanner, the ultrasound image feed comprising ultrasound image frames of a bladder; deploying an AI model to execute on a computing device communicably connected to the ultrasound scanner, wherein the AI model is trained so that when the AI model is deployed, the computing device identifies and predicts a view of the bladder, from one of a sagittal view and a transverse view; acquiring, at the computing device, a new ultrasound image during ultrasound scanning; processing, using the AI model, the new ultrasound image to identify and predict the view of the bladder, wherein the prediction is an AI model output; wherein if the AI model output predicts that the new ultrasound image comprises a sagittal view of the bladder, automatically applying one caliper set along a superior-inferior dimension of the bladder and measuring the superior-inferior dimension; and wherein if the AI model output predicts that the new ultrasound image comprises a transverse view of the bladder, automatically applying two caliper sets along each of a length and a width of the bladder and measuring the length and width thereof.

In another aspect of the present disclosure, there is provided a method for automatically measuring a bladder on an ultrasound image feed which is displayed on a screen that is communicatively connected to an ultrasound scanner, the method comprising activating an AI mode in which the ultrasound scanner obtains an ultrasound signal corresponding to a plurality of ultrasound images of the bladder; freezes one of the plurality of ultrasound images to form a frozen ultrasound image, generates, using the AI model, a prediction of a view of the bladder on the frozen ultrasound image, as between sagittal (longitudinal) and transverse; outputs and employs the prediction of view to apply a correct number of caliper sets on the frozen ultrasound image of the bladder.

In another aspect of the present disclosure, there is provided a method of calculating a bladder volume on an ultrasound image feed, acquired from an ultrasound scanner comprising displaying, on a screen that is communicatively connected to the ultrasound scanner, the ultrasound image feed comprising ultrasound image frames of a bladder; deploying an AI model to execute on a computing device communicably connected to the ultrasound scanner, wherein the AI model is trained so that when the AI model is deployed, the computing device identifies and predicts a view of the bladder, from one of a sagittal view and a transverse view; acquiring, at the computing device, a new ultrasound image during ultrasound scanning; processing, using the AI model, the new ultrasound image to identify and predict the view of the bladder, wherein the prediction is an AI model output; wherein if the AI model output predicts that the new ultrasound image comprises a sagittal view of the bladder, automatically applying one caliper set along a superior-inferior dimension of the bladder and measuring the superior-inferior dimension; rotating the ultrasound scanner and acquiring a subsequent ultrasound image, processing, using the AI model, the subsequent ultrasound image to identify and predict the view of the bladder, wherein the prediction is an AI model output; wherein if the AI model output predicts that the subsequent ultrasound image comprises a sagittal view of the bladder, automatically applying two caliper sets along each of a length and a width of the bladder and measuring the length and width thereof, calculating bladder volume using the superior-inferior dimension, the length and the width.

In another aspect of the present disclosure, there is provided a method of calculating a bladder volume on an ultrasound image feed, acquired from an ultrasound scanner comprising displaying, on a screen that is communicatively connected to the ultrasound scanner, the ultrasound image feed comprising ultrasound image frames of a bladder; deploying an AI model to execute on a computing device communicably connected to the ultrasound scanner, wherein the AI model is trained so that when the AI model is deployed, the computing device identifies and predicts a view of the bladder, from one of a sagittal view and a transverse view; acquiring, at the computing device, a new ultrasound image during ultrasound scanning; processing, using the AI model, the new ultrasound image to identify and predict the view of the bladder, wherein the prediction is an AI model output; wherein if the AI model output predicts that the new ultrasound image comprises a transverse view of the bladder, applying two caliper sets along each of a length and a width of the bladder and measuring the length and width thereof, rotating the ultrasound scanner and acquiring a subsequent ultrasound image, processing, using the AI model, the subsequent ultrasound image to identify and predict the view of the bladder, wherein the prediction is an AI model output; wherein if the AI model output predicts that the subsequent ultrasound image comprises a sagittal view of the bladder, automatically applying one caliper set along a superior-inferior dimension of the bladder and measuring the superior-inferior dimension, calculating bladder volume using the superior-inferior dimension, the length and the width.

In another aspect of the present disclosure, there is provided a method for automatically measuring a bladder on an ultrasound image feed, acquired from an ultrasound scanner comprising acquiring, (preferably in real time), a plurality of ultrasound image frames comprising a bladder, optionally storing the plurality of image frames; deploying an AI model to execute on a computing device communicably connected to the ultrasound scanner, wherein the AI model is trained so that when the AI model is deployed, the computing device identifies and predicts views of the bladder in the plurality of stored ultrasound image frames (for each ultrasound image frame, providing a prediction of a sagittal view or a transverse view); automatically measuring cross-sections of the bladder based on the view predicted by the AI model; wherein if ultrasound image frames of both sagittal view or transverse view are acquired and each respective cross-section measured therefrom, automatically calculating bladder volume. In some aspects of the invention, ultrasound image frames are acquired by freehand scanning and without a requirement for an operator to freeze image frames prior to processing with the AI model. In some aspects of the invention, an operator receives feedback (for example, visually on the display screen or via audio) during scanning indicating whether or not ultrasound image frames comprising both sagittal and transverse views of the bladder are acquired and are of sufficient quality (for example, comprising full bladder in a field of view of such image or images).

In another aspect of the present disclosure, there is provided a method for automatically determining a correction coefficient for calculating bladder volume, which comprises acquiring from an ultrasound scanner a plurality of ultrasound image frames comprising a bladder, predicting a shape of the bladder in one or more of the ultrasound image frames, employing the predicted shape to determine a correction coefficient, automatically calculating bladder volume using the determined correction coefficient.

In another aspect of the present disclosure, there is provided a method for increasing the accuracy of automatic acquisition of cross-sectional measurements of a bladder, in a field of view (FOV) in an ultrasound image, which comprises acquiring from an ultrasound scanner a plurality of ultrasound image frames comprising a bladder, processing the plurality of ultrasound image frames to determine if a bladder is fully/partially shown (and to what degree) in each FOV and what portions of the bladder, if any, are missing in each FOV, wherein if a bladder is only partially shown in FOV: i) adjust one or more scanning and/or processing parameters to increase visibility of cross-sectional measurements in a FOV, in additional imaging frames; and/or ii) provide a user/operator with a margin of error warning pertaining to volume any calculation derived from such ultrasound images.

In another aspect of the present disclosure there is provided an ultrasound imaging system for automatically measuring a bladder on an ultrasound image frame comprising: an ultrasound scanner configured to acquire a new ultrasound image frame; a computing device communicably connected to the ultrasound scanner and configured to process the new ultrasound image frame against a trained AI model to identify and predict a view of the bladder, from one of a sagittal view and a transverse view, on the new ultrasound image frame, to form an AI model output; wherein if the AI model output predicts that the new ultrasound image comprises a sagittal view of the bladder, automatically apply one caliper set along a superior-inferior dimension of the bladder and measure the superior-inferior dimension; wherein if the AI model output predicts that the new ultrasound image comprises a transverse view of the bladder, apply two caliper sets along each of a length and a width of the bladder and measure the length and width thereof; and a display device comprising a screen configured to display the new ultrasound image frame.

In another aspect of the present disclosure, there is provided another system for use in measuring a bladder which comprises an ultrasound scanner and a touchscreen device capable of communicating with the ultrasound scanner, the touchscreen device includes: a processor; and a memory storing instructions for execution by the processor, the interface user trigger for initiating automated measurements of the bladder within an ultrasound image displayed on a touchscreen device, wherein when the instructions are executed by the processor, the processor is configured to: i) receive, via the touchscreen device, direction to acquire measurement of a bladder by receiving inputs of an ultrasound signal of an image displayed on a screen during ultrasound scanning, said image comprising the bladder within a region of interest, ii) apply an AI model to identify and predict a view of the bladder, from one of a sagittal view and a transverse view, on the image, to form an AI model; ii) if the AI model output predicts that the image comprises a sagittal view of the bladder, automatically apply one caliper set along a superior-inferior dimension of the bladder and measure the superior-inferior dimension; iii) if the AI model output predicts that the image comprises a transverse view of the bladder, apply two caliper sets along each of a length and a width of the bladder and measure the length and width thereof; iii) display measurement values on a touchscreen interface viewable by a user; iv) automatically calculate bladder volume using the superior-inferior dimension, the length, the width and a correction co-efficient and display bladder volume on a touchscreen interface viewable by a user.

In another aspect of the present disclosure there is provided computer-readable media storing computer-readable instructions, which, when executed by a processor communicatively coupled with an ultrasound scanner, cause the processor to process, using a trained AI model, a new ultrasound image to identify and predict the view of the bladder, wherein the prediction is an AI model output; wherein if the AI model output predicts that the new ultrasound image comprises a sagittal view of the bladder, automatically apply one caliper set along a superior-inferior dimension of the bladder and measure the superior-inferior dimension; and wherein if the AI model output predicts that the new ultrasound image comprises a transverse view of the bladder, automatically apply two caliper sets along each of a length and a width of the bladder and measure the length and width thereof.

In another aspect of the present disclosure there is provided a computer readable medium storing instruction for execution by a processor communicatively coupled with an ultrasound scanner, within an ultrasound imaging system, wherein when the instructions are executed by the processor, it is configured to: display, on a screen that is communicatively connected to the ultrasound scanner, an ultrasound image feed comprising ultrasound image frames comprising a bladder; activate an AI mode in which the ultrasound scanner obtains an ultrasound signal corresponding to the bladder; generate, using the AI model, a prediction of a view of the bladder as between sagittal (longitudinal) and transverse; output and employ the prediction to automatically apply a correct number of caliper sets on the ultrasound image of the bladder.

In another aspect of the present disclosure, there is provided a touchscreen device which is capable of communicating with an ultrasound scanner, the touchscreen device includes: a processor; and a memory storing instructions for execution by the processor, a interface user trigger for initiating measurements on a bladder within an ultrasound image displayed on a touchscreen device, wherein when the instructions are executed by the processor, the processor is configured to: i) receive, via the touchscreen device, direction to acquire measurement of a bladder by receiving inputs of an ultrasound signal of an image displayed on a screen during ultrasound scanning, said image comprising the bladder within a region of interest, ii) apply an AI model to identify and predict a view of the bladder, from one of a sagittal view and a transverse view, on the image, to form an AI model output; ii) if the AI model output predicts that the image comprises a sagittal view of the bladder, automatically apply one caliper set along a superior-inferior dimension of the bladder and measure the superior-inferior dimension; iii) if the AI model output predicts that the image comprises a transverse view of the bladder, apply two caliper sets along each of a length and a width of the bladder and measure the length and width thereof; and iii) indicate the measurements in a manner accessible by a user (for example, viewable on touchscreen or audible signal or message).

In another aspect of the present disclosure, there is provided a workflow tool for measuring a bladder, enabled by an operator of an ultrasound scanner, in real-time and while scanning, without the need for any additional manual caliper selection, placements or movements. Along with these workflows, the present invention comprises the underlying graphical user interface organized to deploy the method of the invention. This workflow tool may be implemented through an ultrasound scanner, or through a multi-use device communicatively associated with an ultrasound scanner or through an application operated though a cloud-based server communicatively associated with one or both of an ultrasound scanner and a multi-use device. A bladder preset on a graphical user interface organized to deploy the method of the invention may be viewable on a screen, for example a touchscreen, on a multi-use device communicatively associated with an ultrasound scanner.

The present invention provides, in another aspect, one or more output images formed by the method of the present invention. A collection of one or more output images may comprise a visual image product, comprising bladder measurements thereon which may be saved, collected and/or formed into a product such as, for example, a video or other media product for training and reference purposes. It is to be understood that media product as used herein comprises images, and/or videos and/or cineloops and which is rendered using a media rendering program/system, using ultrasound images generated (and optionally labelled, annotated and captioned) using the AI model and measurement module/workflow of the present invention. The media product may be a video written to a physical media (such as a Compact Disc-Recordable (CD-r) or a Digital Video Disc (DVD) or made available online through cloud-based storage, through electronic communication or other transfer and data sharing means. Such media product may comprise, in addition to one or more ultrasound images, annotations and/or text overlays. In some embodiments, the media product may comprise a plurality of cineloops (see, for example, cineloop slider at 624 and play arrow 625 in FIG. 6B and FIG. 6C).

In another broad aspect of the present disclosure, there is provided a server including at least one processor and at least one memory storing instructions for execution by the at least one processor, wherein when executed, the instructions cause the at least one processor to process an ultrasound image frame against an artificial intelligence model to either classify a bladder and/or segment boundaries of a bladder on the ultrasound image frame and then to predict a view of the bladder, from one of a sagittal view and a transverse view, on the ultrasound image frame, to form an AI model output; if the AI model output predicts that the image comprises a sagittal view of the bladder, automatically apply one caliper set along a superior-inferior dimension of the bladder and measure the superior-inferior dimension; if the AI model output predicts that the image comprises a transverse view of the bladder, apply two caliper sets along each of a length and a width of the bladder and measure the length and width thereof; and indicate the measurements in a manner accessible by a user (for example, viewable on touchscreen or audible signal or message).

The system and method of the present invention uses a transducer (e.g., a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

Ultrasound imaging systems are becoming increasingly accessible with many current systems connecting to off-the-shelf display computing devices such as those running iOS™ or Android™ operating systems. These comprise multi-use display devices, such as, for example, tablets and smart phones. As compared to traditional ultrasound systems that have keyboards, a trackball or other physical input controls, these off-the-shelf display computing devices typically receive input via touchscreens. While the use of touchscreen input may allow for a more familiar user interface similar to what is used on consumer devices, it may be difficult to be as precise using touchscreen input versus the physical controls of traditional ultrasound systems.

Within the scope of one preferred aspect of the invention, a bladder may be automatically, and without additional user intervention other than activation of an AI model, identified as to view in an ultrasound image frame and view-specific measurements determined, by a measurement module (wherein two caliper sets are automatically placed on a transverse view of a bladder and one caliper set is placed on a sagittal view of a bladder). In this way, a trained, deployed AI model analyzes signals of an anatomical region of interest, in an ultrasound image frame comprising a bladder as returned to the ultrasound scanner and predicts a view of the bladder as an AI model output. Such an AI model output is then used by the measurement module of the present invention: i) to apply onto the predicted view of the bladder the appropriate number of caliper sets; ii) to acquire measurements from the applied caliper set(s); and optionally iii) to prompt a user to adjust an ultrasound scanner to acquire a secondary view of the bladder so as to ensure both transverse and sagittal views are obtained, and measurements acquired therefrom.

In some embodiments of the invention, ultrasound image frames are B-mode images, and it may be desired to preserve features of these images by applying optional filters thereto. For example, this can be achieved by reducing the noise levels (for example, Salt and Pepper Noise (impulse or spike noise), Poisson noise (shot noise), Gaussian or amplifier noise and Speckle Noise). This reduction may be achieved by use of one or more of the following non-limiting filter types: Gaussian filter, bilateral filter, Order statistic filter, Mean filter and Laplacian filter. It is to be understood that application of such filters is not required.

As such, within the scope of the invention, additional basic parameters for the B-mode (grayscale) examination may preferably be optimized, for the acquisition of higher-quality images. These basic parameters may comprise (a) the location and number of focal zones, (b) the depth of field for the specific vascular feature or ROI being imaged, (c) the two-dimensional (2D) gain setting, (d) the scan orientation, (e) the image zoom settings, and, where possible and depending on the equipment being used, (f) the presets for the specific transducer being used and the type of study being performed.

AI Model

In present invention, an artificial intelligence (AI) model is trained on a plurality of ultrasound images of anatomy/anatomical features, for the purpose of feature classification and/or boundary segmentation as described further below. These images enable the AI model to be trained so that when the AI model is deployed, a computing device communicably connected to an ultrasound scanner, either classifies features, in whole or part or segments boundaries of features, in whole or part, either way thereafter identifying a bladder and further predicting a view of the bladder, as between a sagittal view and a transverse view. As such, the present invention further provides, in another aspect, such a trained and deployable AI model.

There are variety methods which may be employed in AI based segmentation of ultrasound images, and the present invention is not intended to be limited to any one of these methods. Image segmentation refers to the detection of boundaries of features and structures, such as, but not limited to organs, vessels, different types of tissue in ultrasound images. In an embodiment of the present invention, a method deploys a trained AI model to perform intelligent automated recognition of segmentation tasks and intelligent automated selection and application of segmentation algorithms. This allows the AI model to be applied to intelligently perform various different segmentation tasks, including segmentation of different a bladder, in different views. The AI model can intelligently select one or a combination of segmentation algorithms from a plurality of segmentation algorithms to perform appropriate segmentation for various features and anatomical object. For example, the algorithms may be a threshold-based segmentation algorithm, an edge-based segmentation algorithm, a region-based segmentation algorithm, a clustering-based segmentation algorithm, or the like, or a combination thereof.

In some embodiments of the invention, segmentation algorithms may be stored in a segmentation algorithm database which may comprise a plurality of deep learning-based ultrasound image segmentation methods, each of which including a respective trained deep neural network architecture for performing ultrasound image segmentation. For example, the segmentation algorithms can include the deep learning based segmentation algorithms described below, including segmentation using a deep neural network (DNN) that integrates shape priors through joint training, non-rigid shape segmentation method using deep reinforcement learning, segmentation using deep learning based partial inference modeling under domain shift, segmentation using a deep-image-to-image network and multi-scale probability maps, and active shape model based segmentation using a recurrent neural network (RNN). The segmentation algorithm database may include other deep learning-based segmentation algorithms as well, such as marginal space deep learning (MSDL) and marginal space deep regression (MSDR) segmentation methods. It is also possible that a segmentation algorithm database may also store various other non-deep learning-based segmentation algorithms, including but not limited to machine-learning based segmentation methods (e.g., marginal space learning (MSL) based segmentation), graph cuts segmentation methods, region-growing based segmentation methods, and atlas-based segmentation methods.

A segmentation algorithm database may store multiple versions of each segmentation algorithm corresponding to different target anatomical features and structures. For deep learning-based segmentation algorithms, each version corresponding to a specific target anatomical structure may include a respective trained deep network architecture with parameters (weights) learned for segmentation of that target anatomical structure. For a particular anatomical structure, a segmentation algorithm database can also store multiple versions corresponding to different imaging domains and/or image quality levels. For example, different deep learning architectures can be trained and stored using images with different signal-to-noise ratios. Accordingly, when a master segmentation artificial agent selects one or more segmentation algorithms from the those stored in a segmentation algorithm database, the master segmentation artificial agent may select not only the type of segmentation algorithm to apply, but the specific versions of segmentation algorithms that are best for performing the current segmentation task.

In some embodiments, the ultrasound frames of a new ultrasound image, imaged in ultrasound imaging data may be processed against an AI model on a per pixel basis, and thus the segmentation of boundaries of features, in whole or part, on the new ultrasound image, thereby creating one segmented boundary feature or two or more segmented boundary features, imaged in new ultrasound imaging data, may be generated on a per pixel basis. When deployed, an output of the AI model for a first pixel of the new ultrasound imaging data may be used to corroborate the output of the AI model for a second pixel of the new ultrasound imaging data adjacent or within the proximity to the first pixel.

Alternatively, the ultrasound frames of new ultrasound images, imaged in ultrasound imaging data may be processed against an AI model on a line/sample basis, and the and thus the segmentation of boundaries of the feature or features, in whole or part, on the new ultrasound image, thereby creating at least one or two or more segmented boundary features, imaged in new ultrasound imaging data, may be generated on a line/sample basis.

Image segmentation algorithms may automatically identify structures, such as a bladder, in ultrasound images. An example of such a traditional approach is to use an active contours model (also called a "snakes" algorithm) to delineate the outline of the oblong shape visually identified by the ultrasound operator. However, using the active contours model algorithm requires complex mathematical calculations involving the solving of partial differential equations. This is a computationally intensive process. While performing this type of process on a traditional cart-based ultrasound system with high computational and power capacity may not be a problem, executing this type of algorithms on a touchscreen device that connects to an ultra-portable ultrasound scanner may be more difficult. This is because the touchscreen device may be limited in processing ability and battery power; such that executing these types of traditional algorithms on a touchscreen device may result in lower responsiveness in the user interface of the ultrasound application executing on the touchscreen device.

Instead of using a traditional active contours model algorithm, the present embodiments may use a contour identification process that uses morphological operators. For example, to perform morphological processing on an image, an image may first be thresholded to generate a binary image. Then, a structuring element (for example, a small binary configuration of pixels that could be in the shape of a cross or a square) may be positioned at all possible locations of the binary image, to generate a secondary binary image. As each structuring element is positioned over the first binary image, how the structuring element relates to the underlying pixels of the first binary image impacts whether a pixel location is set to '1' or '0' in the secondary binary image.

For example, two common morphological operations are "erosion" and "dilation". In erosion, as the structuring element is positioned over the possible locations of the first binary image, it is required that all the '1' pixels in the first binary image "fit" into the structuring element for the corresponding pixel locations on the second image to be set to '1'. On the edges of any structures appearing on the first binary image, it will generally not be possible to meet this requirement because there will be a combination of '1's and '0's in the structuring element. This will result in some of those pixels that were set to '1' in the first binary image being set to '0' in the second binary image. In this manner, this operation results in a layer of pixels being "eroded" away in the second binary image.

In dilation, as the structuring element is positioned over the possible locations of the first binary image, it is only required that the structuring element "hit" any of the '1' pixels (e.g., that at least one of the pixels in the structuring element is a '1') for the corresponding pixel locations on the second image be set to '1'. On the edges of any structure appearing in the first binary image, there will again generally be a combination of '1's and '0's in the structuring element. However, unlike erosion, the requirement for the structuring element to "hit" a '1' pixel will be met. This will result in some of those pixels that were set to '0' in the first binary image be changed to a '1' in the second binary image. In this manner, this operation results in a layer of pixels being added, and thus the structure in the first binary image is "dilated" in the second binary image.

These types of morphological operators can be used in a contour identification process. For example, a morphological snakes algorithm is similar to the traditional active contours model or "snakes" algorithm, except that morphological operators (e.g., dilation or erosion) are used to grow or shrink the contour. Since morphological operators operate generally on binary images, operations can be performed over a binary array instead of over a floating-point array (as would be the case if a traditional active contours model or "snakes" process is used). Thus, using a contour identification process that uses morphological operators may be considered less computationally intensive, and such processes may be particularly suitable for execution with ultrasound scanners that connect to mobile touchscreen devices that generally have lower computational capabilities and operate on battery power. This mode of contour identification is described in U.S. Pat. No. 11,593,937, the entire contents of which are incorporated herein by reference.

Measurement Module/Workflow

In some embodiments, the present invention additionally comprises a measurement module which receives an output of the AI model, which is a predicted view of a bladder in an ultrasound image frame, and i) applies onto the image of the bladder the appropriate number of caliper sets; and ii) acquires measurements from the applied caliper set(s). Additionally, the measurement module may automatically calculate bladder volume using the acquired measurements.

Additionally, the measurement module may automatically prompt a user to adjust an ultrasound scanner to acquire a secondary view of the bladder in additional ultrasound image frames so as to ensure both transverse and sagittal views are obtained, in order for measurements may be acquired from both views in order to calculate bladder volume.

The present invention addresses an issue of automatic and accurate caliper placement on a bladder during scanning and overcomes human errors associated with improper caliper placement.

In one aspect of the invention, one or more measurements and/or calculated bladder volume(s) are displayed visually on an interface, such as an interface on a multi-purpose electronic device. This visual display may provide, for example the actual measurement numbers (one or more of the superior-inferior dimension, the length, and the width) encircled or in a prominent, easy to view area of the interface. This visual display may provide, for example the actual calculated bladder volume at or near one or more of the measurement numbers. In another aspect of the invention, the one or more measurement numbers may be conveyed to a user audibly. In using presets or other AI enhancement modules, such an interface may also convey to a user, visually or audibly, the AI model identified/predicted view of the bladder being scanned and subsequently the measurements thereafter acquired.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

The system of the present invention uses a transducer (e.g., a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

A user input device may comprise one or more of a touchscreen, a keyboard, a mouse, a trackpad, a motion sensing camera, or other device configured to enable a user to interact with and manipulate data within image processing system. In one example, user input device may enable a user to make a selection of an ultrasound image to use in training an AI model, or for further processing using a trained AI model. A display device may include one or more display devices utilizing virtually any type of technology. In some embodiments, display device may be part of a multi-purpose display device or may comprise a computer monitor, and in both cases, may display ultrasound images. A display device may be combined with processor, non-transitory memory, and/or user input device in a shared electronic device, or there may be peripheral display devices which may comprise a monitor, touchscreen, projector, or other display device known in the art, which may enable a user to view ultrasound images produced by an ultrasound imaging system, and/or interact with various data stored in non-transitory memory.

Figure 13:
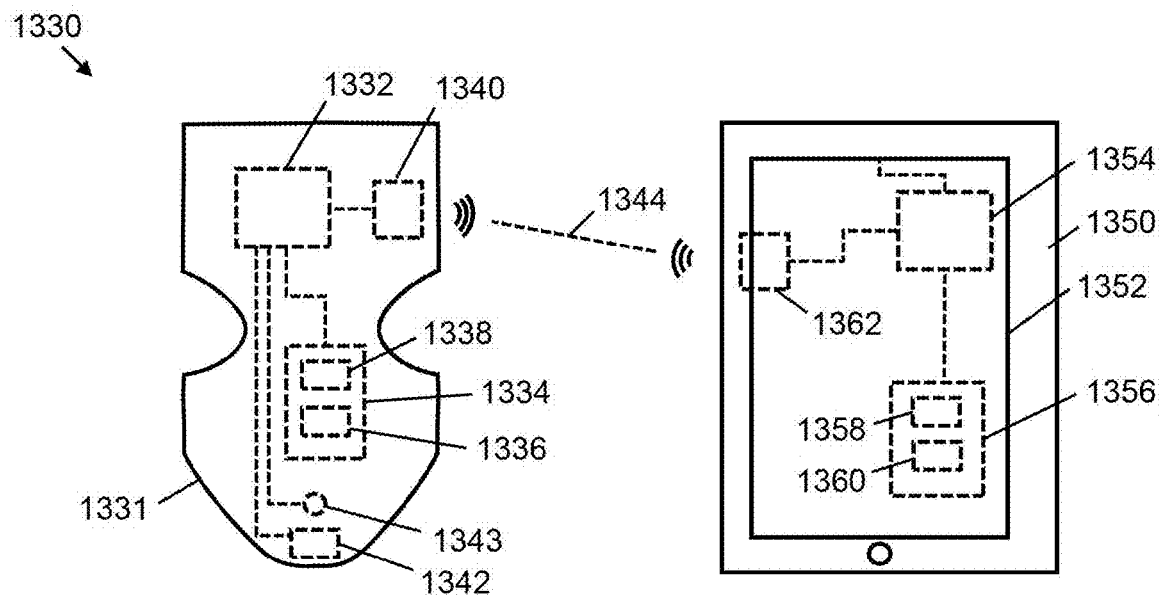
FIG. 13 is a schematic diagram of an ultrasound imaging system, according to an embodiment of the present invention.
Figure 14:
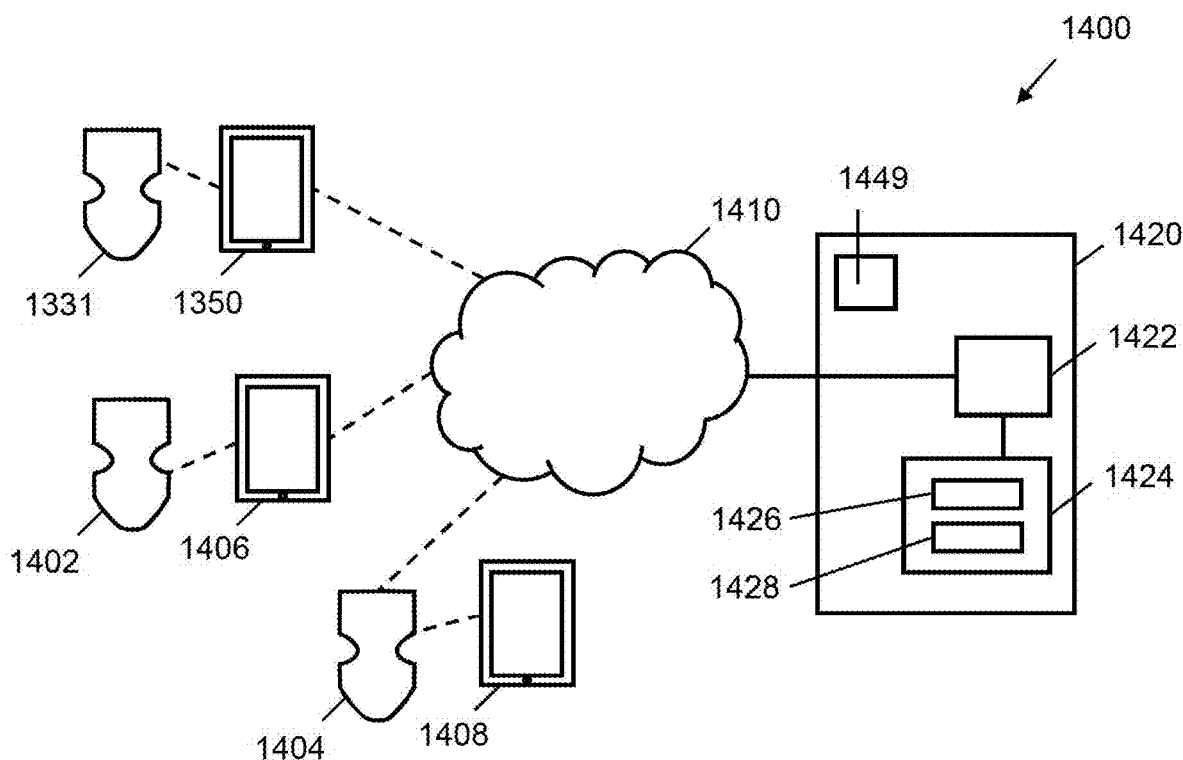
FIG. 14 is a schematic diagram of a system with multiple ultrasound scanners, according to an embodiment of the present invention.

In various embodiments, a multi-purpose electronic devices/display devices may be, for example, a laptop computer, a tablet computer, a desktop computer, a smart phone, a smart watch, spectacles with a built-in display, a television, a bespoke display or any other display device that is capable of being communicably connected to an ultrasound probe. Multi-purpose electronic devices/display devices may host a screen (such as shown in FIGS. 13 and 14), and may include a processor, which may be connected to a non-transitory computer readable memory storing computer readable instructions, which, when executed by the processor, cause the display device to provide one or more of the functions of the system (such system comprising at least one multi-purpose electronic device and at least probe). Such functions may be, for example, the receiving of ultrasound data that may or may not be pre-processed; scan conversion of received ultrasound data into an ultrasound image; processing of ultrasound data in image data frames; the display of a user interface; the control of a probe and the display of an ultrasound image on the screen. Such a screen may comprise a touch-sensitive display (e.g., touchscreen) that can detect a presence of a touch from the operator on screen and can also identify a location of the touch in screen. The touch may be applied by, for example, at least one of an individual's hand, glove, stylus, or the like. As such, the touch-sensitive display may be used to receive an input, for example, indicating the presence or absence of text or annotations on an image. The screen and/or any other user interface may also communicate audibly. Multi-purpose electronic devices/display devices may be configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory within the multi-purpose electronic devices/display devices may be computer readable data which may be used by processors within multi-purpose electronic devices/display devices, in conjunction with the computer readable instructions within multi-purpose electronic devices/display devices 1350, 1406, 1408, to provide the functions of the system. Such computer readable data may include, for example, settings for ultrasound probe, such as presets for acquiring ultrasound data and settings for a user interface displayed on screens. Settings may also include any other data that is specific to the way that the ultrasound probe operates or that multi-purpose electronic devices/display devices operate.

Referring to FIG. 1, there is shown a flowchart diagram of a method, generally indicated at 100, of new image frame acquisition of a region of interest comprising a bladder; deploying an AI model to execute on a computing device communicably connected to the ultrasound scanner, wherein the AI model is trained so that when the AI model is deployed, the computing device identifies and predicts for the new imaging frame, a view of the bladder, from one of a sagittal view and a transverse view, wherein the prediction is an AI model output; wherein if the AI model output predicts that the new ultrasound image comprises a sagittal view of the bladder, automatically applying one caliper set along a superior-inferior dimension of the bladder and measuring the superior-inferior dimension; and wherein if the AI model output predicts that the new ultrasound image comprises a transverse view of the bladder, applying two caliper sets along each of a length and a width of the bladder and measuring the length and width thereof, according to at least one embodiment of the present invention. At 110, the ultrasound imaging system (e.g., as referred to in FIGS. 13 and 14), may acquire ultrasound imaging data in the form of an imaging frame. For example, a user may operate an ultrasound scanner (hereinafter "scanner", "probe", or "transducer" for brevity) to capture images of a patient. The ultrasound frames (B-mode) may be acquired by acquiring a series of a images (with a frame each containing a sequence of transmitted and received ultrasound signals) of different views of the abdominal region. The performance of the bladder AI model within the scope of the invention is optimized by the removal of common ultrasound artifacts like an acoustic shadow, lateral shadow, anisotropic effect, reverberation, and refraction. As these artifacts are common in bladder ultrasound, users may optionally adopt one or more of the following techniques to reduce these artifacts during use, such as, for example: scanning from different angles and planes and ensuring the anatomy of interest is centered and in focus.

Further, at step 112, a new ultrasound imaging frame may optionally be pre-processed and/or augmented. In some embodiments, an optional pre-processing act may be performed on the new ultrasound image frame to facilitate improved performance and/or accuracy when training the machine learning (ML) algorithm and when deploying the machine learning (ML) algorithm through the AI model. For example, it may be possible to pre-process the ultrasound imaging frame through a high contrast filter to reduce the granularity of greyscale on the ultrasound image. Additionally, or alternatively, it may be possible to reduce scale of the ultrasound image frame prior to providing the ultrasound image frame for processing through the AI model at step 114. Reducing the scale of ultrasound image frame as a preprocessing step may reduce the amount of image data to be processed, and thus may reduce the corresponding computing resources required. Various additional or alternative pre-processing acts may be performed. For example, these acts may include data normalization to ensure that the various ultrasound imaging frame has the dimensions and parameters which are optimal for processing through the AI model.

Figures 7A, 7B, 7C:
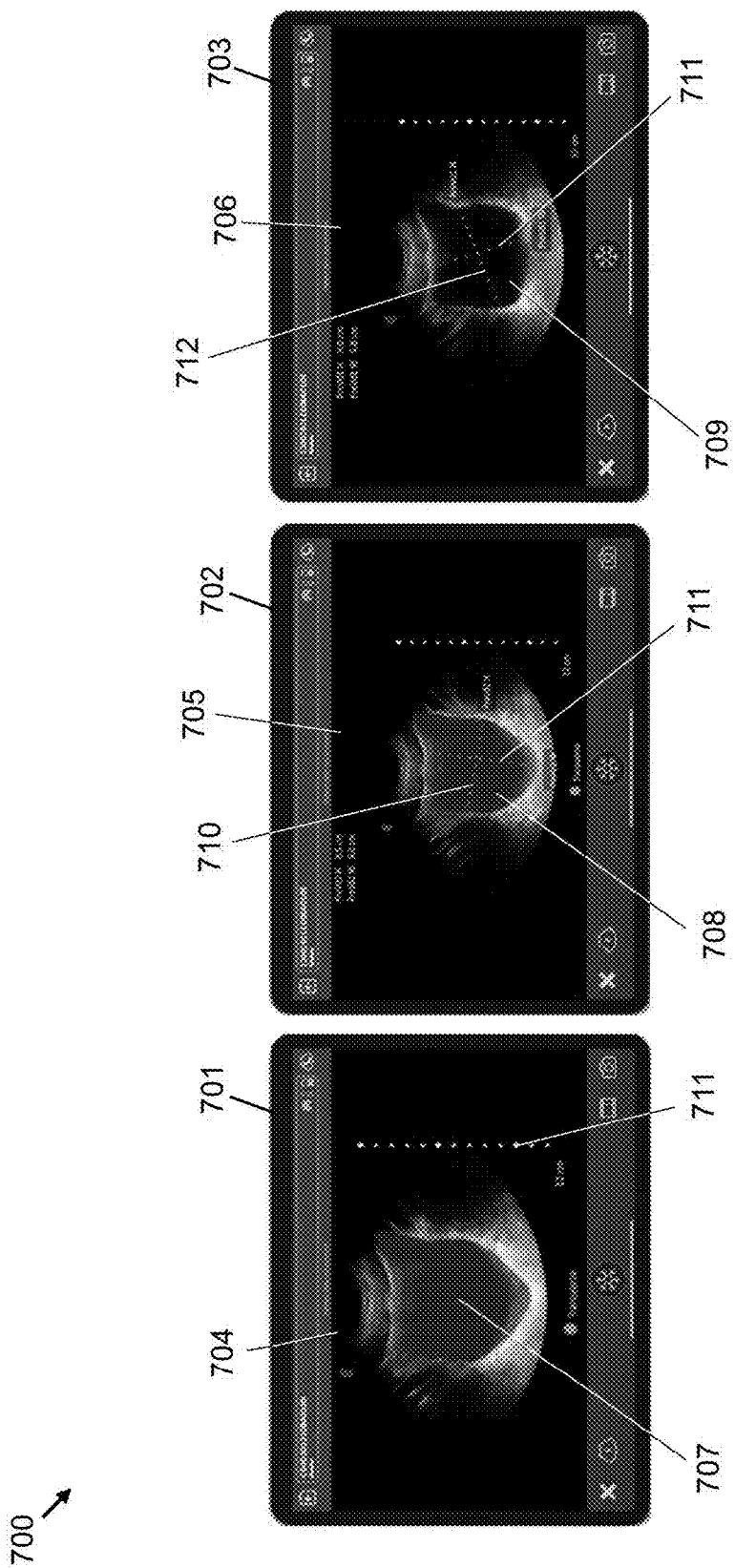
FIG. 7A is an image showing the result of performing acts of the present methods on an example ultrasound image, in accordance with at least one embodiment of the present invention.
FIG. 7B is an image showing the result of performing acts of the present methods on an example ultrasound image, in accordance with at least one embodiment of the present invention.
FIG. 7C is an image showing the result of performing acts of the present methods on an example ultrasound image, in accordance with at least one embodiment of the present invention.

At step 114, the new ultrasound imaging frame/image data is processed with an AI model so that at step 116, a view of the bladder in the ultrasound image frame is identified and predicted. As described herein, such identification and prediction my be achieved by a variety of methods, including, but not limited to, segmentation of boundaries/edge detection, contouring and classification. This invention is not intended to be limited to any one mode of AI-model-generated bladder identification. The product of the AI model is an output prediction at step 118 of a bladder view, as shown in the ultrasound image frame. The output is automatically conveyed to a measurement module at step 120 which, based on the output/predicted view, automatically places a correct number of caliper sets on the bladder in the ultrasound image frame at step 122. The caliper set is placed along at least one longest length of the bladder, in the ultrasound imaging frame. For example, as shown in FIGS. 6B and 6C, for a predicted sagittal view, one caliper set is automatically and correctly placed across the longest cross section of the bladder in this view (shown as hatched line 620 between two boundary points). For example, as shown in FIGS. 7B and 7C, for a predicted transverse view, two caliper sets are automatically and correctly placed across the two longest cross-sections of the bladder in this view (shown as hatched line 710 between two boundary points and 711 between two other boundary points). The measurement module of the present invention deploys the correct number of caliper sets at the correct location points on the image of the bladder, on the ultrasound image frame, based on the predicted view output of the AI model.

Referring still to FIG. 1, step 124 directs that steps 110 to 122 may be repeated as necessary for additional images and for additional views. For example, if the new imaging frame comprised a bladder which was predicted to be a sagittal view, one or more additional images may be acquired to capture of a bladder in transverse view, for additional processing through steps 110 to 122.

Figure 2:
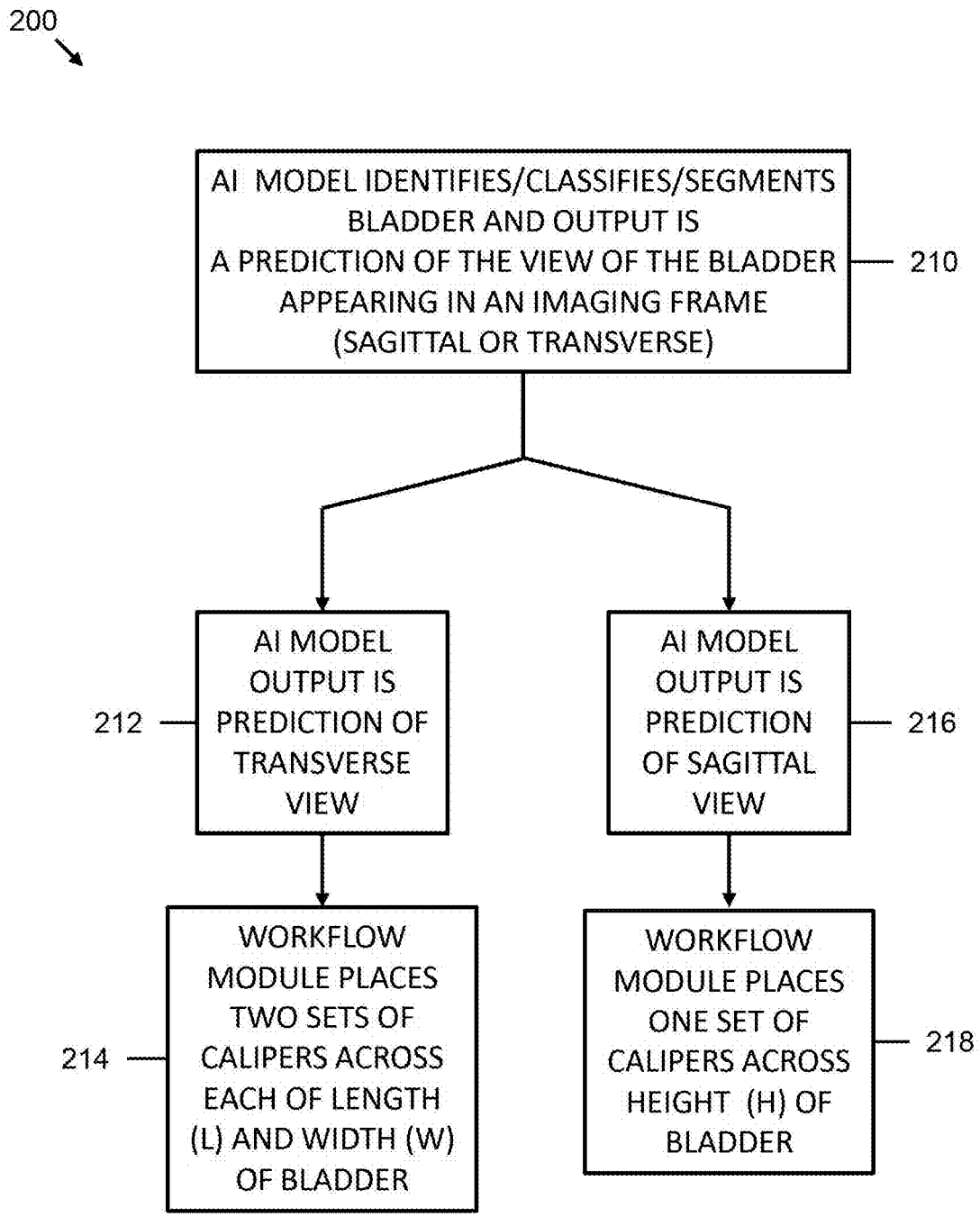
FIG. 2 is another flowchart diagram showing steps of a method, performed by a workflow module, of automatically performing caliper placement on an AI model predicted view of a bladder, on an ultrasound image displayed on a device, in accordance with at least one embodiment of the present invention.

Disposition of the correct number of caliper sets, across the correct cross-sections on a bladder image is additionally shown a flowchart diagram of a method, generally indicated at 200, in FIG. 2. At step 210, a trained AI model identifies a bladder (by one of a variety of methods including, for example, segmentation and classification etc.) and predicts a view of the identified bladder which is the output of the AI model. If the AI model predicts that the view of the bladder in the ultrasound image frame is transverse (at step 212), a workflow module receiving that output at step 214 automatically places two sets of calipers across each of the a length (L) and a width (W) of the bladder, each of such calipers extending a lines, perpendicular to each and other and intersecting at a centre point of the bladder (see, for example FIGS. 7B and 7C). Alternatively, if the AI model predicts that the view of the bladder in the ultrasound image frame is sagittal (at step 216), a workflow module receiving that output at step 218 automatically places only one caliper set of calipers across a superior-inferior dimension of the bladder as shown, for example, in FIGS. 6C and 6C.

Figure 3:
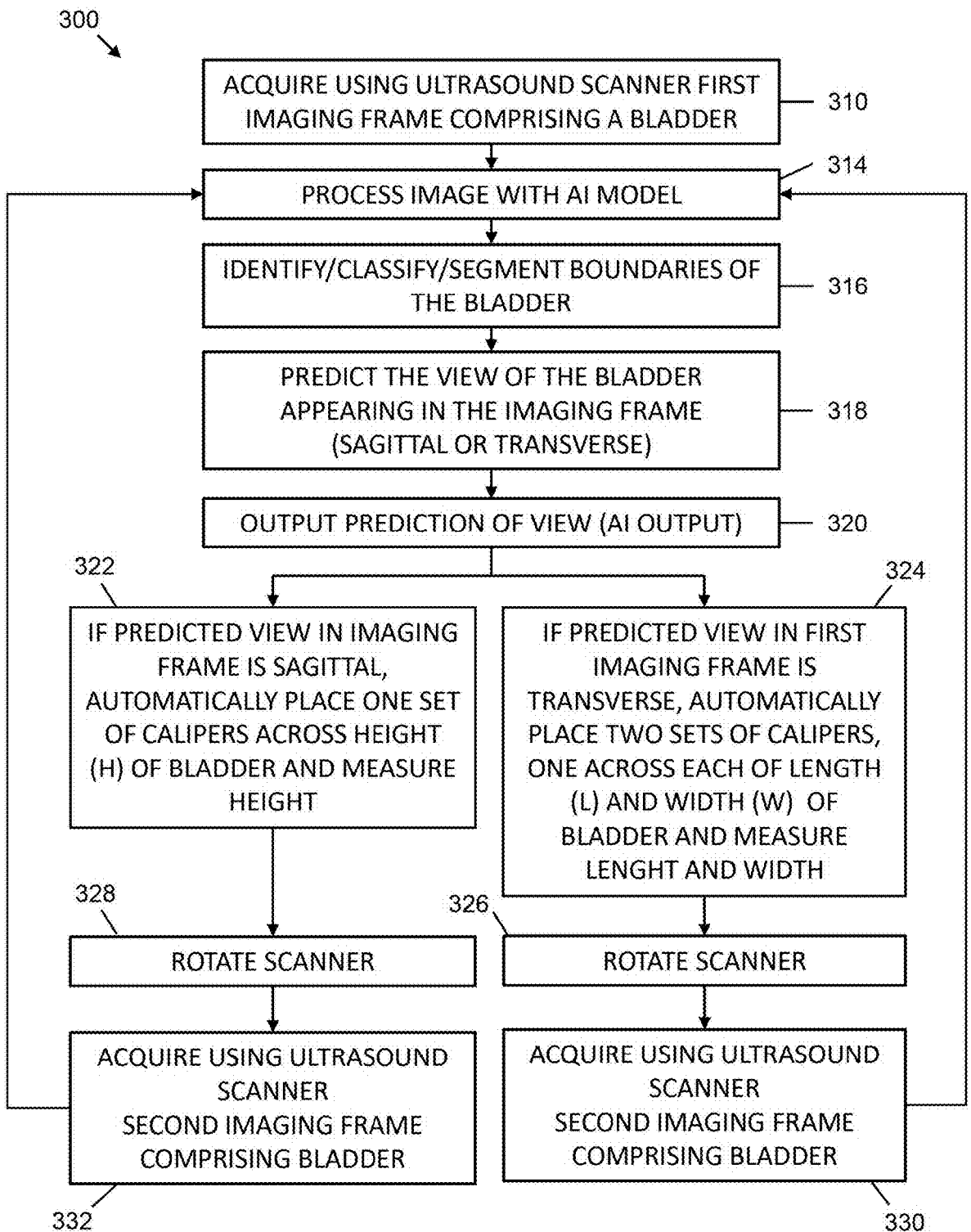
FIG. 3 is another flowchart diagram showing sequential steps of acquiring an ultrasound image of a bladder, deploying a trained AI model to identify the bladder and predict its view, and then a processor receiving the output of the AI model and automatically performing caliper placement on the AI model predicted view of a bladder, in accordance with at least one embodiment of the present invention.

In order to calculate a bladder volume, cross-sectional measurements from both a transverse view of the bladder and sagittal view of the bladder are required. Referring to FIG. 3, there is shown a flowchart diagram of a method, generally indicated at 300, of acquiring (using an ultrasound scanner) and processing, using the method of the present invention, a first imaging frame, in one view and subsequently acquiring and processing a second imaging frame from a view different from the view in the first imaging frame, so that all three cross-sectional measurements can be acquired. More specifically, at step 310 a first imaging frame of a bladder/region of interest comprising a bladder is acquired using an ultrasound scanner and processed, at step 314, with a trained AI model. At step 316, the AI model identifies the bladder and at step 318, predicts the view of the bladder appearing in the imaging frame (sagittal or transverse). The output of the AI model at step 320 is a predicted view. If the predicted view in the imaging frame is sagittal, one set of calipers is appropriately placed at step 322 across the superior-inferior dimension. AI model output predicts that the new ultrasound image comprises a sagittal view of the bladder, automatically applying one caliper set along a superior-inferior dimension (also referred to as "height" of the bladder) and measuring the superior-inferior dimension. A user may then rotate or be prompted to rotate the ultrasound scanner 90 degrees (e.g., counterclockwise) at step 328 so as to acquire, at step 332, a second imaging frame comprising the bladder. If the first imaging frame is predicted to be a sagittal view, the rotation prior to the acquisition of further images will enable a user to capture a second imaging frame which may be predicted to be a transverse image, after completion of steps 314-324. If the predicted view in the imaging frame (from steps 318 and 320) is a transverse view, two sets of calipers are appropriately placed at step 324 (one across each of the length and the width) and each is measured. A user may then rotate or be prompted to rotate the ultrasound scanner 90 degrees (e.g., clockwise) at step 326 so as to acquire, at step 330, a second imaging frame comprising the bladder. If the first imaging frame is predicted to be a transverse view, the rotation prior to the acquisition of further images will enable a user to capture a second imaging frame which may be predicted to be a sagittal image, after completion of steps 314-322.

Figure 4:
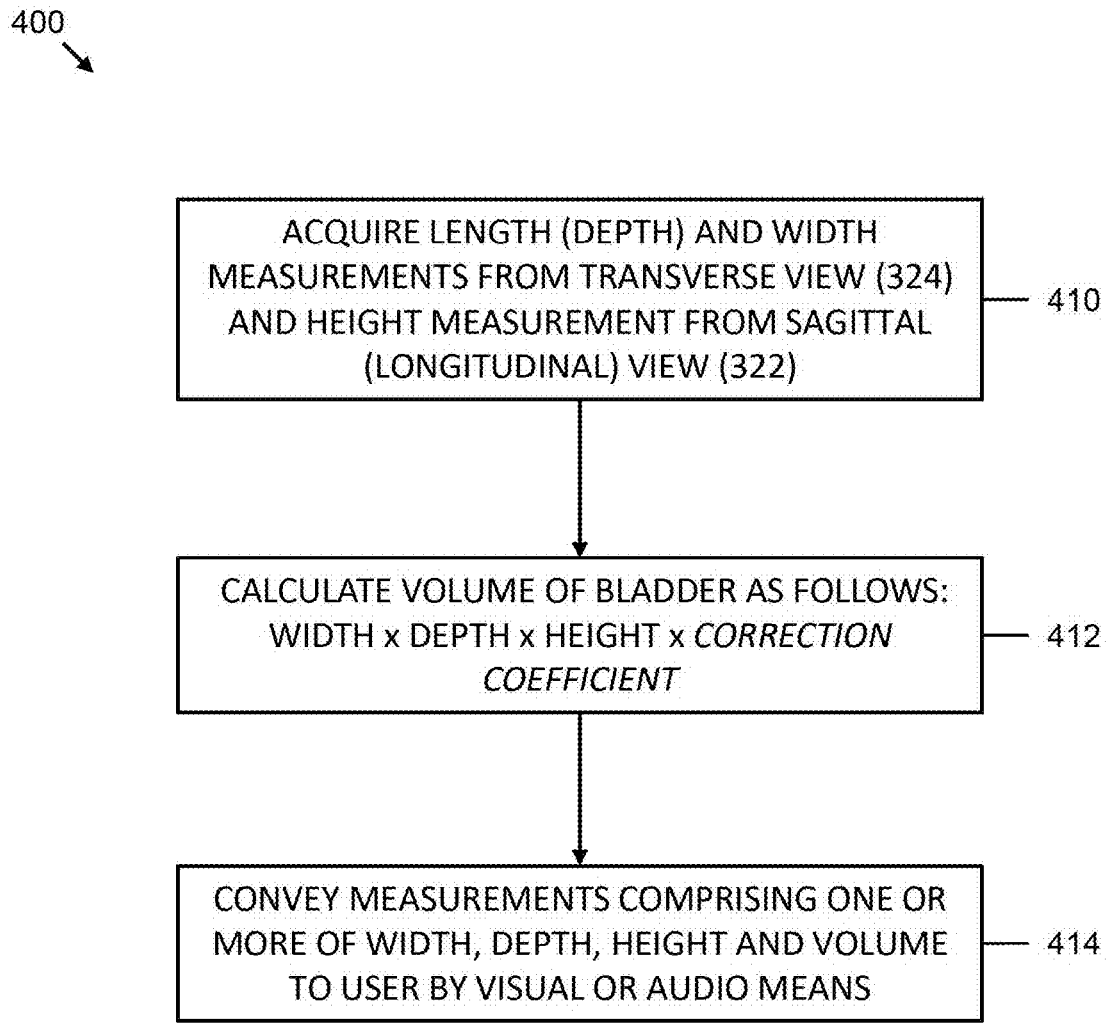
FIG. 4 is another flowchart diagram showing the steps of bladder volume calculation.

Calculation of bladder volume is illustrated in FIG. 4, with the acquisition at step 410 of length (referred to also as depth) and width measurements from a transverse view and a longitudinal (also referred to as height or superior-inferior dimension) from a sagittal view and the multiplication by the measurement module of these collective measurements by a correction co-efficient (CC):

$$W \times D \times H \times CC = \text{BLADDER VOLUME (step 412)}$$

For general volume estimation, linear regression analysis yields optimal correction coefficients of 0.72 for unknown/general data set data set but for a greater degree of accuracy, the shape of a bladder may be accounted for by the measurement module of the present invention in selecting a specific correction co-efficient, i.e., the correction coefficient that most closely corresponds to the patient's bladder shape. Table 1 displays correction coefficients for each of the common bladder shapes set out graphically in FIG. 9:

TABLE 1

| Bladder Shape | Correction Coefficient |
| --- | --- |
| Unknown | 0.72 (most commonly used) |
| Triangular prism (910) | 0.66 |
| Cylinder (Ellipsoid) (912) | 0.81 |
| Cuboid (914) | 0.89 |
| Spherical (916) | 0.52 |

Figure 9:
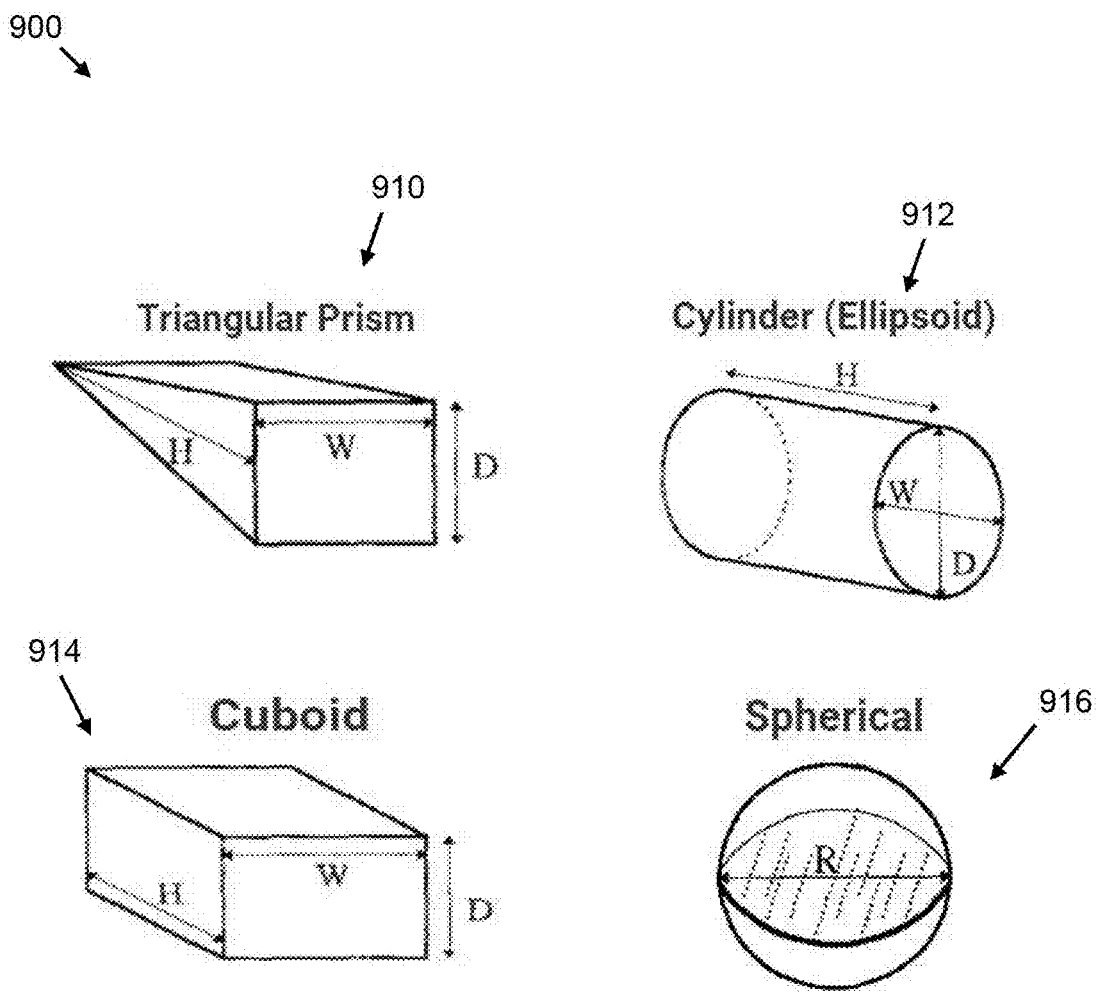
FIG. 9 is an illustration of generally known bladder shapes.

For example, a volume of a bladder may be estimated by orthogonal measurements, assuming it to be an ellipsoid (correction coefficient×the three orthogonal dimensions). Both pre- and post-void ultrasound image measurements should be taken to diagnose urinary retention. In one aspect of the present invention, an additional trained AI model may be deployed to identify a shape of a bladder, for the purpose of automatically applying the most suitable correction coefficient in the measurement module of the present invention. In another aspect of the invention, the measurement module automatically applies a correction coefficient of 0.72 unless a user inputs another correction co-efficient. In yet another aspect of the invention, a correction coefficient other than 0.72 is applied by default based on prior imaging of the patient/subject. In yet another aspect of the invention, one or more correction coefficients are built into bladder AI presets and applied according to relative height, width and depth measurements. FIG. 9 further depicts these relative measurements, on each shape.

Referring back to FIG. 4, at step 414, measurements comprising one or more of width, depth, height and volume are conveyed to a user. This conveyance may be visually through numeric indicators on a display interface screen (such as shown for example in FIGS. 6B, 6C, 7B and 7C) or conveyance may be by audio signals. Generally, and by way of example only, an entire bladder volume should be less than 300-400 mL in healthy adults and Post Void Residual (PVR) should be less than 50-100 mL in healthy adults. Practically, the goal of volume calculation in many instances is to determine if a patient is retaining urine and knowing the precise volume with a high degree of accuracy may not matter, depending on use context.

FIGS. 5A, 5B and 5C are schematics of exemplary user interface displays, each setting out progression of a method, in accordance with one aspect of the invention, for initiating the deployment of the trained AI model, shown generally at 500. In FIG. 5A, at interface screen 501, there is displayed frozen image 504 comprising bladder 507. A user pauses the acquisition of ultrasound image frames by pressing freeze button 514. A selection of icons at the left of interface screen 501 includes an AI icon 508, which, once selected, activates bladder detection and highlighting. The AI icon is further highlighted by the yellow arrow. Additional icons include image appearance icon at 509 and overall gain icon at 510. At FIG. 5B, on interface screen 502, in addition to displayed image 505 comprising bladder 518, a circular carousel is viewable with all available AI models from which a user may make a selection. By way of example, shown are the Clarius AI App 520 and the model for "Bladder Volume" 519, the latter of which, when selected, activates the AI model. In FIG. 5C, on interface screen 503, once the AI is activated, AI button 508 changes colour and/or offer a visual "on" indicator. Interface screen 503 additionally shows displayed image 506 comprising bladder 522. Interface screens 501/502/503 may additionally comprise one or more controls and guides including but not limited to: imaging mode selector 513, freeze button 514, video icon 515, screen capture icon 516, tools icon 512 and depth indicator 511.

FIGS. 6A, 6B and 6C illustrate bladder segmentation and automatic caliper placement for a sagittal view, shown generally at 600. AI icon 608 is indicated as being activated. Additional adjacent icons include image appearance icon at 609 and overall gain icon at 610. Once the AI model is activated, and bladder 607 is in view in displayed image 604, on interface screen 601, the AI segmented bladder is automatically highlighted by a yellow mask on top, as shown in FIGS. 6A and 6B. As an output of the AI model is the prediction of a sagittal view of bladder 618 in displayed image 605, one caliper set 620 is placed automatically across the longest axis in view. These calipers will be placed automatically depending on the predicted view from the AI model, with measurements calculated automatically and shown in the top left corner of the screen. Once all three measurements (length, height, width) have been captured, the calculated bladder volume may be automatically displayed on the screen. To remove the segmentation mask over bladder 622 on displayed image 606, and disable the AI, as shown in FIG. 6C, a user simply taps AI button 608 and selects "Bladder Volume" (see 519 in FIG. 5B) from the AI carousel wheel which will turn the AI button white. Although within this example, an orange-coloured AI button signifies on, whereas a white coloured AI button signifies off, there are other visuals, graphics and schematics which may indicate the status/operational state of the AI model to a user. The segmentation mask can also be disabled in freeze mode. Once the image acquisition is frozen, the AI model may be disabled by tapping the button (toggle on/off as described). This is particularly useful for users who want to see the bladder (optionally with placed calipers) but without the segmentation mask overlay. In FIG. 6C, the segmentation mask has been removed from bladder 622 on displayed image 606, displayed on interface screen 603 and a single caliper set has been automatically placed by the measurement module. Interface screens 601/602/603 may additionally comprise one or more controls and guides including but not limited to: imaging mode selector 613, freeze button 614, video icon 615, screen capture icon 616, tools icon 612 and depth indicator 611. Slider icon 624 shows playback and scrolling of cineloop and 625 is a cineloop play icon. Information bar 630 may comprise status information including type of scanner in use, battery levels, and other information pertinent to user.

Referring to FIGS. 7A, 7B and 7C, there is shown a similar progression as FIGS. 6A, 6B and 6C, but illustrate bladder segmentation and automatic caliper placement for a transverse view, shown generally at 700. In each case (FIG. 6A/B/C and FIG. 7A/B/C), calipers sets are automatically placed based upon the AI model output and create points to provide diameter measurements of each cross-section (e.g., two for transverse view, one for sagittal view). For example, on a transverse view, these are two points on the bladder contour or segmentation mask with the longest distance on a line parallel to (or small slope against) the horizontal axis. Once the AI model is activated, and bladder 707 is in view in displayed image 704, on interface screen 701, the AI segmented bladder is automatically highlighted by a yellow mask on top, as shown in FIGS. 7A and 7B. As an output of the AI model is the prediction of a transverse view of bladder 708 in displayed image 705 (on interface screen 702 in FIG. 7B), two caliper sets (710 and 711) are placed automatically across the two longest axes in view. These calipers may be placed automatically depending on the predicted view from the AI model, with measurements calculated automatically and shown in the top left corner of the screen. To remove the segmentation mask over bladder 708 on displayed image 705, and disable the AI, as shown in FIG. 7C, a user simply taps AI button 508 and selects "Bladder Volume" (see controls 508 and 519 in FIG. 5B). FIG. 7C, the segmentation mask has been removed from bladder 709 on displayed image 706, displayed on interface screen 703, and two calipers sets have been automatically placed by the measurement module of the present invention.

Figures 8A, 8B, 8C:
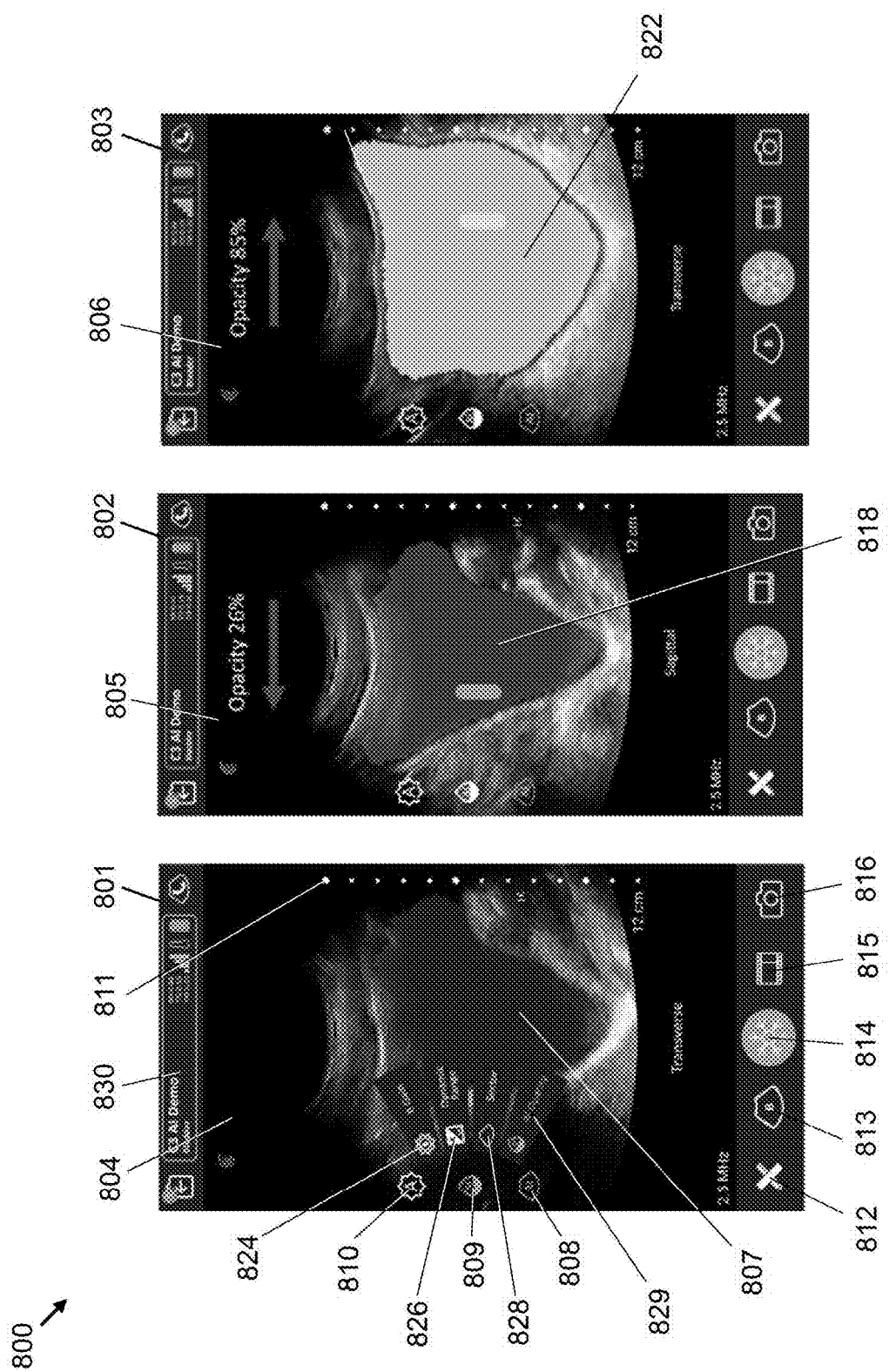
FIG. 8A is an image showing the result of performing acts of the present methods on an example ultrasound image, in accordance with at least one embodiment of the present invention.
FIG. 8B is an image showing the result of performing acts of the present methods on an example ultrasound image, in accordance with at least one embodiment of the present invention.
FIG. 8C is an image showing the result of performing acts of the present methods on an example ultrasound image, in accordance with at least one embodiment of the present invention.

The opacity of a segmentation mask can also be adjusted as shown generally as 800 in FIGS. 8A, 8B and 8C. In FIG. 8A, at interface screen 801, there is displayed image 804 comprising segmented bladder 807. A selection of icons at the left of interface screen 801 includes an AI icon 808, image appearance icon 809 and overall gain icon 810. Activation of slider control 809 exposes a carousel wheel exposing icons for AI opacity 829, sector 828, dynamic range 826 and B gain 824. Adjustments to opacity are enabled through user activation of the AI opacity icon 829 and interface sliding scale adjustments as depicted in FIGS. 8B (displayed image 805 comprising segmented bladder 818) and 8C (displayed image 806 comprising segmented bladder 822). Scroll directions are highlighted by the red arrows in FIG. 8B (opacity decreasing to 265) and 8C (opacity increasing to 85%). Opacity is displayed on the images upon change. Interface screens 801/802/803 may additionally comprise one or more controls and guides including but not limited to: imaging mode selector 813, freeze button 814, video icon 815, screen capture icon 816, tools icon 812 and depth indicator 811.

Figure 10:
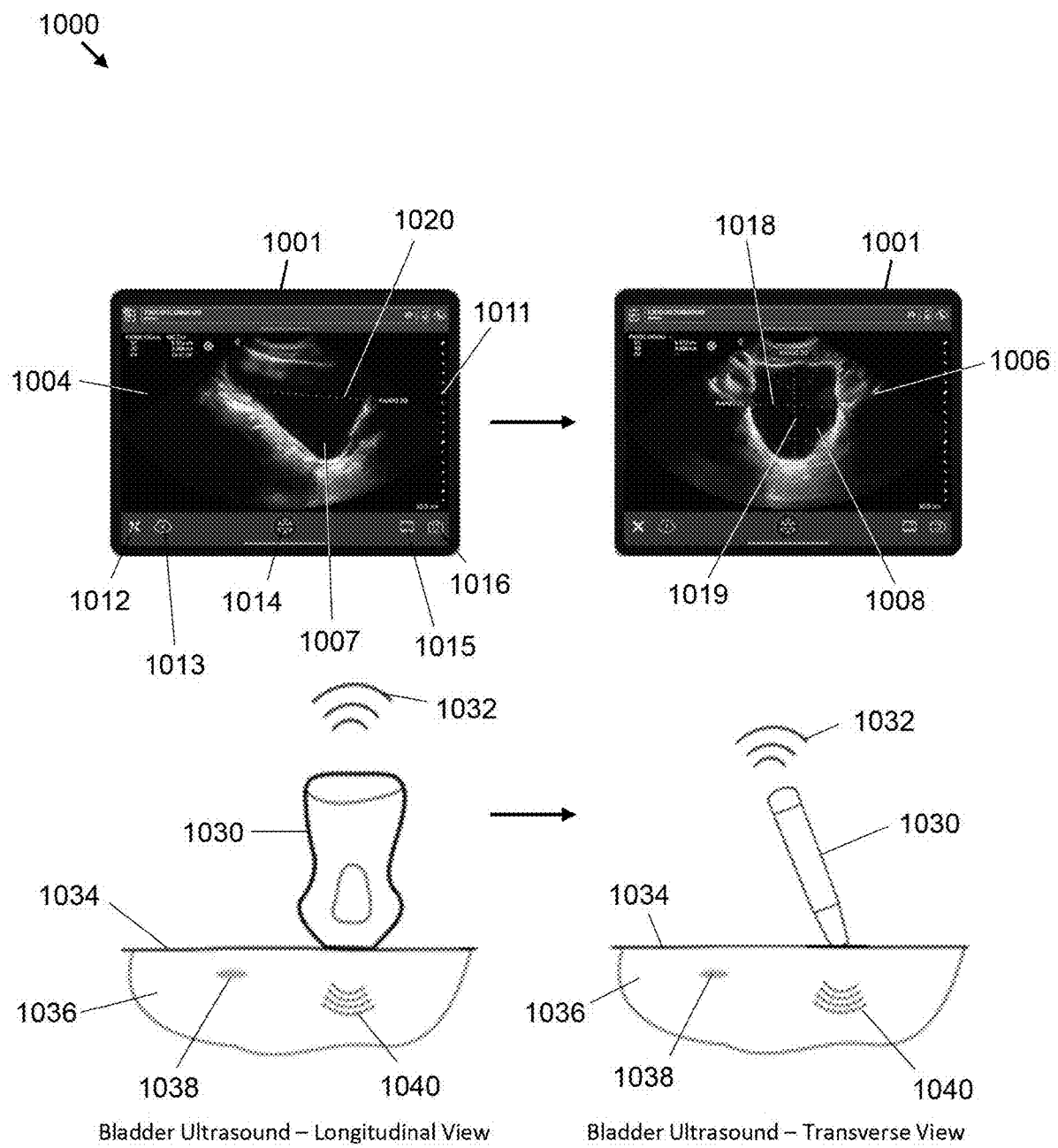
FIG. 10 is a schematic of a depiction of motion, both as ultrasound image frames displayed on a screen, with respective view of an ultrasound scanner positioned over a patient, showing acquisition and capture of an ultrasound image frame of a bladder in a longitudinal view and then subsequent rotation of the probe to acquire and capture a secondary view, a transverse view, in accordance with at least one embodiment of the present invention.

Ultrasound images for use within the method and system of the invention may be acquired during examination of a patient in supine position with suprapubic area exposed. An ultrasound probe is placed longitudinally in the mid-line above the pubic symphysis with probe marker towards patient's head to obtain a first view (generally sagittal) of the bladder. The probe may be angled laterally and fanned (tilted) to left and right to acquire images of the lateral borders. FIG. 10 depicts the acquisition of a first image, in a sagittal view, for processing in accordance with the method of the present invention and then probe is rotated 90 degrees counterclockwise to obtain a transverse view, for processing in accordance with the method of the present invention. Generally, at 1000, FIG. 10 represents a visual of the motion of a probe to acquire both sagittal (longitudinal) and transverse views of the bladder, in order to gather all measurements for volume calculation. Ultrasound scanner 1030 rotates counterclockwise 90 degrees over skin 1034 of patient 1036, as indicated by the directional arrow. A marker on the patient skin, shown for example as a belly button 1038 provides a visual cue that the scanner (and not patient) is rotating. Activation/scanning mode is depicted in the figures with ultrasonic waves under the patient skin and wireless communication between the ultrasound scanner and display device 1001 is depicted by universal wireless signal 1032. Display device 1001 offers a screen interface 1004 for viewing the sequential ultrasound images which have been acquired, frozen, processed using an AI model to identify a bladder and predict its view and then automatically applied with a correct caliper set or sets, dependent on view predicted by the AI model. Screen interface 1004 may additionally comprise one or more controls and guides including but not limited to: imaging mode selector 1013, freeze button 1014, video icon 1015, screen capture icon 1016, tools icon 1012 and depth indicator 1011.

In a first orientation, (left side graphics) of FIG. 10, probe 1030 acquires a plurality of primary ultrasound images frames, at least one of which is frozen (1004), using freeze button 1014. Using the procedure described above, an AI model is activated, and the view of bladder 1007 is predicted (here, for image 1004, it is a predicted sagittal view). The output enables a workflow to automatically place one caliper set across line 1020. After rotation, probe 1030 acquires a plurality of secondary ultrasound images frames, at least one of which is frozen (1006), using freeze button 1014. The AI model is activated, and the view of bladder 1008 is predicted (here, for 1006, it is a predicted transverse view). The output enables a workflow to automatically place two caliper sets across lines 1018 and 1019. With that, all three measurement points are collected and automatically used by the measurement tool/measurement module of the present invention to calculate and display bladder volume.

As described herein, in the deployment of the AI model of the invention, identification and prediction may be achieved by a variety of methods, including, but not limited to, segmentation of boundaries/edge detection, contouring and classification. This invention is not intended to be limited to any one mode of AI-model-generated bladder identification. The product of the AI model is an output prediction (for example at step 118 in FIG. 1) of a bladder view, as shown in the ultrasound image frame. The output is automatically conveyed to a measurement module at step 120 which, based on the output/predicted view, automatically places a correct number of caliper sets on the bladder in the ultrasound image frame at step 122.

In various embodiments, a variety of means to segment an ultrasound image may be used. For example, segmentation may be performed by dividing it into multiple parts or regions that belong to the same class. This task of clustering is based on specific criteria, for example, color or texture and is referred to as pixel-level classification. This involves partitioning images into multiple segments or objects using techniques including, but not limited to 1) thresholding, wherein a threshold value is set, and all pixels with intensity values above or below the threshold are assigned to separate regions; 2) region growing, wherein an ultrasound image is divided into several regions based on similarity criteria. This segmentation technique starts from a seed point and grows the region by adding neighboring pixels with similar characteristics; 3) edge-based segmentation wherein segmentation techniques are based on detecting edges in the ultrasound image and these edges represent boundaries between different regions that are detected using edge detection algorithms; 4) clustering, wherein groups of pixels are clustered based on similarity criteria. These criteria can be color, intensity, texture, or any other feature; 5) active contours, also known as snakes, wherein curves that deform are used to find the boundary of an object in an image. These curves are controlled by an energy function that minimizes the distance between the curve and the object boundary; 6) deep learning-based segmentation, such as by employing Convolutional Neural Networks (CNNs), which employ a hierarchical approach to image processing, where multiple layers of filters are applied to the input image to extract high-level features, the training of which is described herein in FIGS. 11 and 12.

Figure 11:
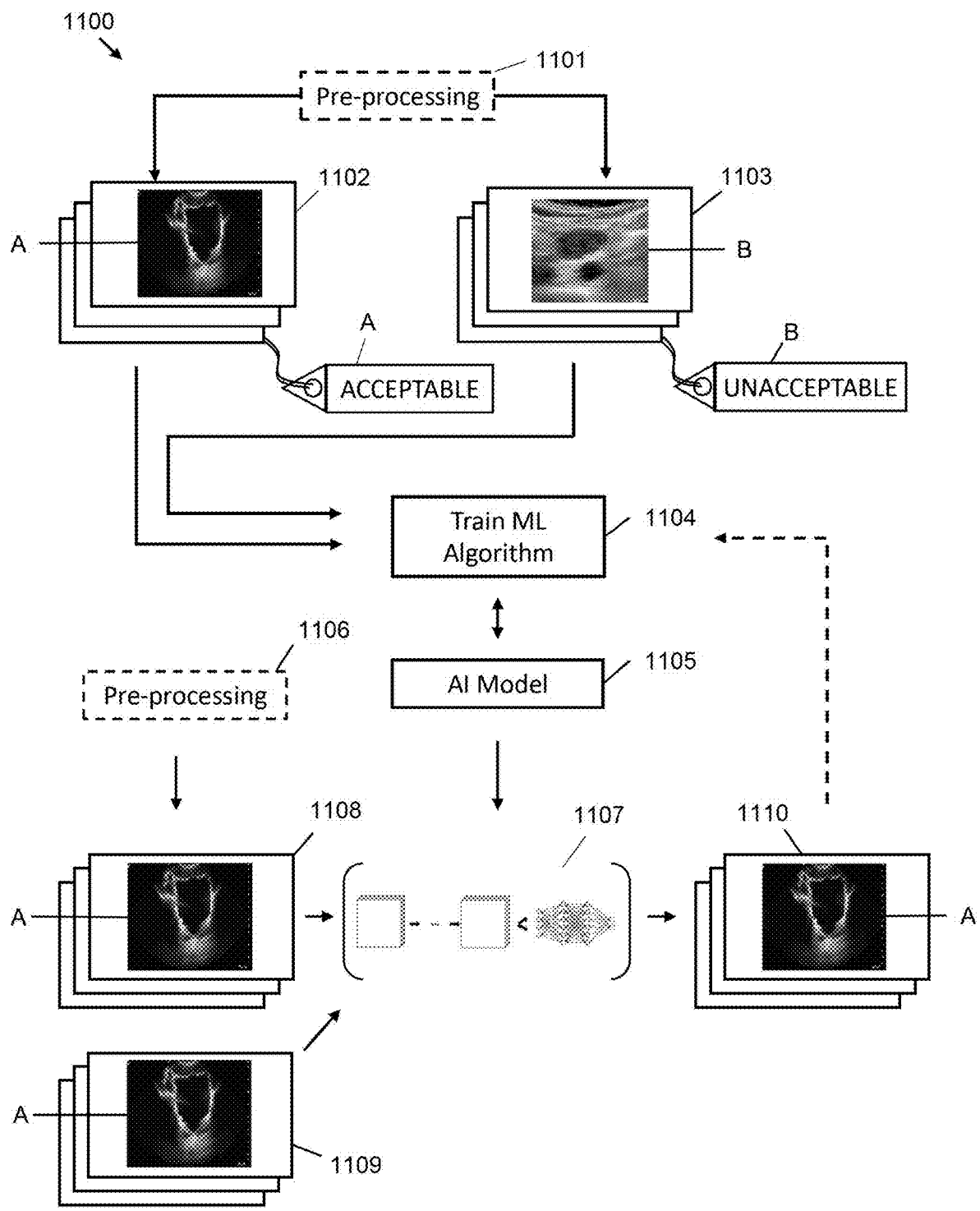
FIG. 11 is a schematic diagram of the training and deployment of an AI model, according to an embodiment of the present invention.

Referring to FIG. 11, shown there generally at 1100 is a schematic diagram of a training and deployment of an AI model 1105. According to an embodiment of the present invention, there is shown a method of training a neural network 1107 to so that when the AI model is deployed, a computing device identifies and segments boundaries of features, in whole or part. Specifically, during use and deployment, neural network 1107 identifies, in a new ultrasound image, optimal bladder boundary delineation, in an ultrasound image frame.

For training, a number of ultrasound frames of a ROI (in whole view, from varying perspectives and parts thereof) may be acquired using an ultrasound scanner (hereinafter "scanner", "probe", or "transducer" for brevity). The ultrasound frames may be acquired by fanning a series of a planes (with a frame each containing a sequence of transmitted and received ultrasound signals), through an angle and capturing a different ultrasound frame at each of a number of different angles. During the scanning, the scanner may be held steady by an operator of the scanner while a motor in the head of the scanner tilts the ultrasonic transducer to acquire ultrasound frames at different angles. Additionally, or alternatively, other methods of acquiring a series of ultrasound frames may be employed, such as using a motor to translate (e.g., slide) the ultrasonic transducer or rotate it, or manually tilting, translating or rotating the ultrasound scanner.

The AI model if preferably trained with a robust selection of images of varying views. For example, these different views may include transverse plane views of a ROI, including views from different angles that combine any of a sagittal plane view, a coronal plane view, or a transverse plane view. In these embodiments, the scanner may be placed in an arbitrary orientation with respect to the ROI, provided that the scanner captures at least a portion of the ROI.

In some embodiments, ultrasound scans of a ROI, for training, may be acquired from medical examinations. During the scans, images may be obtained; however, for training of the AI model of the invention, non-clinically useful or acceptable images may also be used.

Referring still to FIG. 11, training ultrasound frames (1102 and 1103) may include ultrasound frames with features that are tagged as acceptable (A) and representative of images which are segmented and most advantageously boundaries of a bladder or alternatively are tagged respectively as unacceptable (B) and unrepresentative of such division and segmentation. By way of example, in ultrasound frame 1102, which is marked as acceptable, there is provided a bladder image which is marked as correctly and at least adequality segmented and identified. Conversely, ultrasound frame 1103, of the same ROI as ultrasound frame 1102, is marked as unacceptable, due to the fact that the features are unclear, and/or unclear and/or are at least non-adequality segmented.

Figure 12:
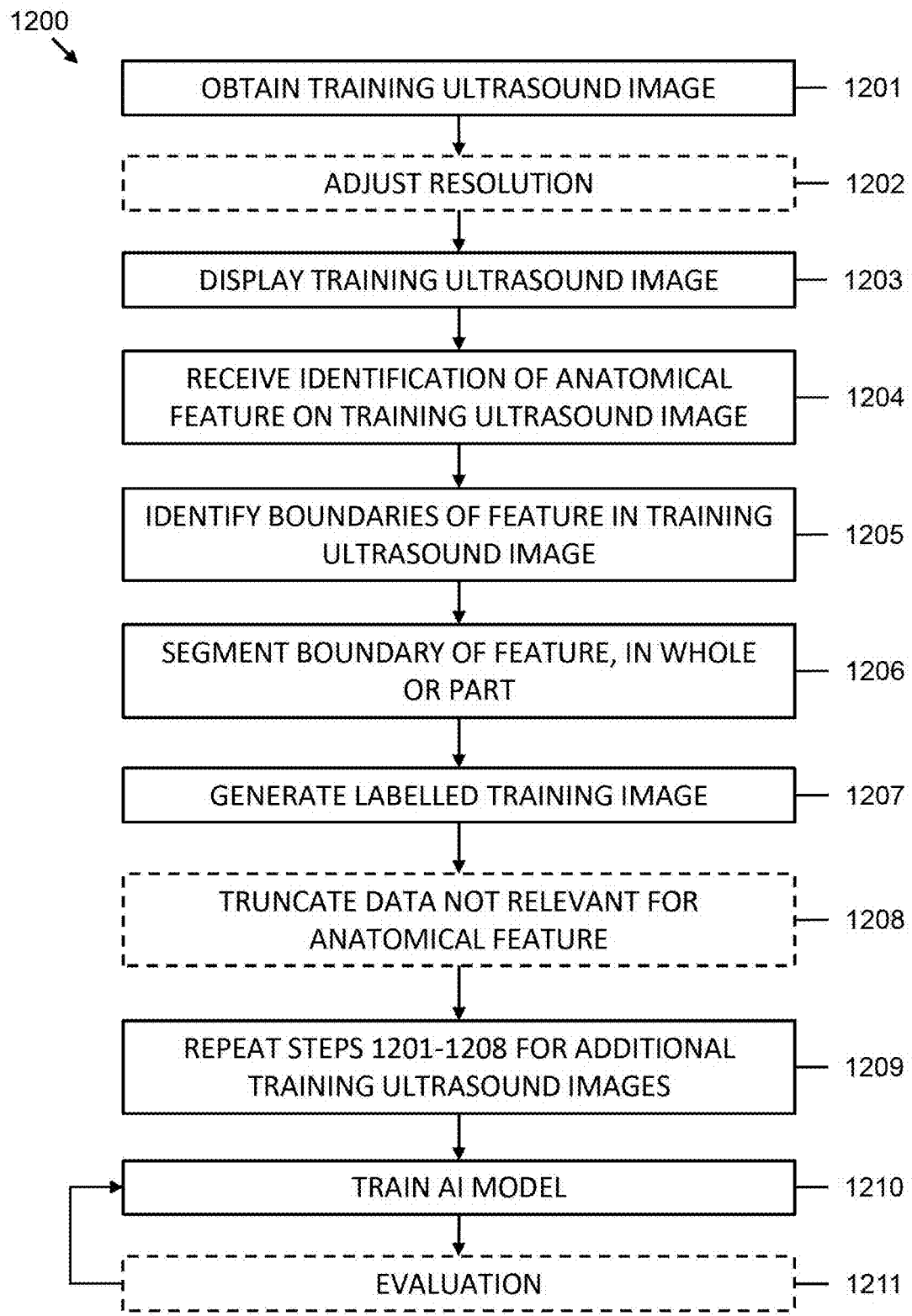
FIG. 12 is flowchart diagram of the steps for training the AI model, according to an embodiment of the present invention.

Both the training ultrasound frames labeled as Acceptable and Unacceptable, for each particular ROI (whole or part), may themselves be used for training and/or reinforcing AI model 1105. This is shown in FIG. 12 with tracking lines from both 1011 to training algorithm step 1210. As such, ultrasound frame 1103 may be employed for training as an unacceptable image.

In some embodiments, an optional pre-processing act 1101 may be performed on the underlying ultrasound image frames 1102 and 1103 to facilitate improved performance and/or accuracy when training the machine learning (ML) algorithm. For example, it may be possible to pre-process the ultrasound images 1102 and 1103 through a high contrast filter to reduce the granularity of greyscale on the ultrasound images 1102 and 1103.

Additionally, or alternatively, it may be possible to reduce scale of the ultrasound images 1102 and 1103 prior to providing the ultrasound images 1102 and 1103 to the training algorithm step 1104. Reducing the scale of ultrasound images 1102 and 1103 as a preprocessing step may reduce the amount of image data to be processed during the training act 1104, and thus may reduce the corresponding computing resources required for the training act 1104 and/or improve the speed of the training act 1104.

Various additional or alternative pre-processing acts may be performed in act 1101. For example, these acts may include data normalization to ensure that the various ultrasound frames 1102 and 1103 used for training have generally the same dimensions and parameters.

Referring still to FIG. 11, the various training frames 1102 and 1103 may, at act 1104, be used to train a ML algorithm. For example, the various training ultrasound frames 1102 and 1103, may be inputted into deep neural network 1107 that can learn how to predict boundaries of features in new ultrasound images as compared to all trained and stored images.

The result of the training may be the AI model 1105, which represents the mathematical values, weights and/or parameters learned by the deep neural network to predict segmented boundaries of features, within a ROI, in whole or part. The training act 1104 may involve various additional acts (not shown) to generate a suitable AI model 1105. For example, these various deep learning techniques such as regression, classification, feature extraction, and the like. Any generated AI models may be iteratively tested to ensure they are not overfitted and sufficiently generalized for creating the comparison and list of probabilities in accordance with method of the invention.

In some embodiments, using a cross-validation method on the training process would optimize neural network hyper-parameters to try to ensure that the neural network can sufficiently learn the distribution of all possible image types without overfitting to the training data. In some embodiments, after finalizing the neural network architecture, the neural network may be trained on all of the data available in the training image files.

In various embodiments, batch training may be used, and each batch may consist of multiple images, thirty-two for example, wherein each example image may be gray-scale, preferably 128*128 pixels although 256*256 pixels and other scaled may be used, without any preprocessing applied to it.

In some embodiments, the deep neural network parameters may be optimized using the Adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behaviour. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent over-fitting and add more transitional invariance to the model. Therefore, in some embodiments, the training images may be augmented on-the-fly while training. In every mini-batch, each sample may be translated horizontally and vertically, rotated and/or zoomed, for example. The present invention is not intended to be limited to any one particular form of data augmentation, in training the AI model. As such, any mode of data augmentation which enhances the size and quality of the data set and applies random transformations which do not change the appropriateness of the label assignments may be employed, including but not limited to image flipping, rotation, translations, zooming, skewing, and elastic deformations.

Referring still to FIG. 11, after training has been completed, the sets of parameters stored in the storage memory may represent a trained neural network of a plurality of images of ROIs which identifies and segments boundaries of features with each ROI, in whole or part.

In order to assess the performance of AI model 1105, the stored model parameter values can be retrieved any time to perform image assessment through applying an image to the neural networks (shown as 1107) represented thereby. In some embodiments, the deep neural network may include various layers such as convolutional layers, pooling layers, and fully connected layers. In some embodiments, the final layers may include a softmax layer as an output layer having outputs which eventually would demonstrate respective determinations that an input set of pixels fall within a particular area above or below a feature boundary, in the training images. Accordingly, in some embodiments, the neural network may take at least one image as an input and output a binary mask indicating which pixels belong to the area above a feature boundary (or part thereof), e.g., the AI model classifies which area each pixel belongs to.

To increase the robustness of the AI model 1105, in some embodiments, a broad set of training data may be used at act 1104. For example, it is desired that ultrasound images of a plurality of different ROIs, across a plurality of anatomical regions in a body, in whole and a variety of parts thereof, from views including but not limited to coronal and/or transverse plane views, including views from different angles that combine any of a sagittal plane view, a coronal plane view, or a transverse plane view.

More specifically, training images 1102 and 1103 may be labeled with one or more features associated with/are hallmarks of a particular ROI, including key anatomical features therein. This may include identifying a variety of features visualized in the captured training image. In at least some embodiments, this data may be received from trainer/user input. For example, a trainer/user may label the features relevant for the application visualized in each training image.

The image labeling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper and accurate feature identification. For example, this can include training ultrasound images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, training ultrasound images 1102 and 1103 can include a graduation of training images ranging from images with just sufficient image quality to high image quality. In this manner, the machine learning model may be trained to identify features on training medical images that have varying levels of sufficient image quality for later interpretation and probability assessment.

Overall, the scope of the invention and accorded claims are not intended to be limited to any one particular process of training AI model 1105. Such examples are provided herein by way of example only. AI model 1105 may be trained by both supervised and unsupervised learning approaches although due to scalability, unsupervised learning approaches, which are well known in the art, are preferred. Other approaches may be employed to strengthen AI model 1105.

The image labelling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper and accurate feature identification. For example, this can include training ultrasound images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, training medical images can include a graduation of training medical images ranging from images with just sufficient image quality to high image quality. In this manner, the machine learning model may be trained to identify features on training medical images that have varying levels of sufficient image quality for later interpretation and probability assessment.

Turning back to FIG. 11, once a satisfactory AI model 1105 is generated, the AI model 1105 may be deployed for execution on a neural network 1107 to identify and segment boundaries of features, in whole or part, within a ROI. Notably, the neural network 1107 is shown in FIG. 11 for illustration as a convolution neural network—with various nodes in the input layer, hidden layers, and output layers. However, in various embodiments, different arrangements of the neural network 1107 may be possible.

In various embodiments, prior to being processed for analysis as described herein, training ultrasound image frames may optionally be pre-processed in a manner analogous to the pre-processing act 112 in FIG. 1. (e.g., processing through a high contrast filter and/or scaling), to facilitate and improve accuracy in identifying and selecting boundaries of features, in whole or part.

The training images file may include an image identifier field for storing a unique identifier for identifying an image included in the file, a segmentation mask field for storing an identifier for specifying the to-be-trimmed area, and an image data field for storing information representing the image.

Referring again to FIG. 11, once a satisfactory AI model 1105 is generated, the AI model 1105 may be deployed for execution on a neural network 1107 to segment a bladder, as described fully herein, new ultrasound images 1108. Notably, the neural network 1107 is shown in FIG. 11 for illustration as a convolution neural network—with various nodes in the input layer, hidden layers, and output layers. However, in various embodiments, different arrangements of the neural network 1107 may be possible.

In various embodiments, prior to being processed for feature segmentation, the new ultrasound images 1108 may optionally be pre-processed. This is shown in FIG. 11 with the pre-processing act 1106 in dotted outline. In some embodiments, these pre-processing acts 1106 may be analogous to the pre-processing acts 1101 performed on the training ultrasound frames 1102 and 1103 (e.g., processing through a high contrast filter and/or scaling), to better align the new ultrasound images 1108 with the training ultrasound image frames, and thereby facilitate improved accuracy in feature segmentation. For example, pre-processing an input image may help standardize the input image so that it matches the format (e.g., having generally the same dimensions and parameters) of the training ultrasound images 1102 and 1103 that the AI model 1105 is trained on.

In various embodiments, the new ultrasound images 1108 may be live images acquired by an ultrasound imaging system (e.g., the system discussed with respect to FIGS. 13 and 14 below). For example, the AI model 1105 may be deployed for execution on the scanner 1331 and/or the display device 1350 discussed in more detail below. Additionally, or alternatively, the AI model 1105 may be executed on stored (as opposed to new) ultrasound images 1109 that were previously acquired (e.g., as may be stored on a Picturing Archiving and Communication System (PACS)).

Whether the images are stored ultrasound images 1109 or new ultrasound images 1108, the AI model 1105 enables the neural network 1107 to properly segment a feature within a ROI imaged in the new/stored ultrasound imaging data and created an identified and segmented bladder image frame 1110.

FIG. 12 is flowchart diagram of the steps, generally indicated as 1200, for training the AI model of FIG. 11, according to an embodiment of the present invention. In some embodiments, method 1200 may be implemented as executable instructions in any appropriate combination of the imaging system 1330 (FIG. 13), for example, an external computing device connected to the imaging system 1330, in communication with the imaging system 1330, and so on. As one example, method 1200 may be implemented in non-transitory memory of a computing device, such as the controller (e.g., processor) of the imaging system 1330.

Referring still to FIG. 12, in step 1201, a training ultrasound image may be obtained. For example, a training ultrasound image may be acquired by the scanner 1331 (as shown in FIG. 13) transmitting and receiving ultrasound energy. The training ultrasound image may generally be a post-scan converted ultrasound image. While the method of FIG. 12 is described in relation to a single training ultrasound image, the method may also apply to the use of multiple training ultrasound images. While the method of FIG. 12 is described in relation to a post-scan ultrasound image, it is to be understood that pre-scan images, may be used, as described in U.S. patent application Ser. No. 17/187,851 filed Feb. 28, 2021, the entire contents of which are incorporated herein by reference.

Optionally, in step 1202 (as shown in dotted outline), the resolution of the training ultrasound image may be adjusted. For example, the resolution may be increased or decreased. The purpose of this may be to provide the labeler (e.g., a medical professional with relevant clinical expertise) with training ultrasound images that have a more standardized appearance. This may help to maintain a higher consistency with which the labeler identifies anatomical features in the training ultrasound images. Besides the resolution, other parameters of the training ultrasound image may also be adjusted such as input scaling, screen size, pixel size, aspect ratio, and the removal of dead space, as described above (including, for example, data augmentation and other pre-processing steps).

In step 1203, the training ultrasound image may be displayed on a display device, such as the display device 1350 discussed in more detail below in relation to FIG. 13. The labeler can then identify a particular anatomy in the training ultrasound image by, for example, tagging it with a name from a pull-down menu or by using other labeling techniques and modalities. The labeler then can mark the training ultrasound image around the particular anatomy that the labeler has identified in the training ultrasound image. In step 1204, the system that is used for the training may receive the identification of the anatomical feature(s) on the training ultrasound image. In step 1205, the system may generate, for example, from a labeler's marking inputs, identified boundaries of a feature or features in the training ultrasound frame. In step 1206, a boundary feature is segmented in order to, at step 1207, generate a labeled training image.

In various embodiments, steps may readily be interchanged with each other. For example, the generation of labeled confirmation at step 1207 may automatically proceed, without trainer intervention, using prior data which directs to the placement of feature boundaries.

Once the training ultrasound image has been segmented and labeled, the system may then remove, in step 1208, optionally, (as shown in dotted outline), regions of the labeled ultrasound data frame that are both outside the area of the identified boundary features and outside areas relevant for the AI model to recognize the particular anatomy within the ROI. For example, the labeled ultrasound data frame may be truncated at one or more sides. Truncation of some of the ultrasound data may allow the training of the AI model to proceed more quickly. There is provided a redirection at step 1209 to repeat steps 1201-1208 a plurality of times, for additional training images. At step 1210, AI model is trained. At step 1211, once training is completed, the AI model may be used to perform identifications and selections on an unseen dataset to validate its performance, such evaluation at step 1211 feeding data back to train the AI model at step 1210.

Referring to FIG. 13, an exemplary system 1330 is shown for predicting a view of a bladder on an ultrasound image acquired from an ultrasound scanner, and then automatically placing the correct number of calipers, in accordance with such the predicted view. The system 1330 includes an ultrasound scanner 1331 with a processor 1332, which is connected to a non-transitory computer readable memory 1334 storing computer readable instructions 1336, which, when executed by the processor 1332, may cause the scanner 1331 to provide one or more of the functions of the system 1330. Such functions may be, for example, the acquisition of ultrasound data, the processing of ultrasound data, the scan conversion of ultrasound data, the transmission of ultrasound data or ultrasound frames to a display device 150, the detection of operator inputs to the ultrasound scanner 131, and/or the switching of the settings of the ultrasound scanner 131.

Also stored in the computer readable memory 1334 may be computer readable data 1338, which may be used by the processor 1332 in conjunction with the computer readable instructions 1336 to provide the functions of the system 1330. Computer readable data 1338 may include, for example, configuration settings for the scanner 1331, such as presets that instruct the processor 1332 how to collect and process the ultrasound data for a plurality of ROIs and how to acquire a series of ultrasound frames. The scanner 1331 may include an ultrasonic transducer 1342 that transmits and receives ultrasound energy in order to acquire ultrasound frames. The scanner 1331 may include a communications module 1340 connected to the processor 1332. In the illustrated example, the communications module 1340 may wirelessly transmit signals to and receive signals from the display device 1350 along wireless communication link 1344. The protocol used for communications between the scanner 1331 and the display device 1350 may be WiFi™ or Bluetooth™, for example, or any other suitable two-way radio communications protocol. In some embodiments, the scanner 1331 may operate as a WiFi™ hotspot, for example. Communication link 1344 may use any suitable wireless communications network connection. In some embodiments, the communication link between the scanner 1331 and the display device 1350 may be wired. For example, the scanner 1331 may be attached to a cord that may be pluggable into a physical port of the display device 1350.

In various embodiments, the display device 1350 may be, for example, a laptop computer, a tablet computer, a desktop computer, a smart phone, a smart watch, spectacles with a built-in display, a television, a bespoke display or any other display device that is capable of being communicably connected to the scanner 1331. The display device 1350 may host a screen 1352 and may include a processor 1354, which may be connected to a non-transitory computer readable memory 1356 storing computer readable instructions 1358, which, when executed by the processor 1354, cause the display device 1350 to provide one or more of the functions of the system 1330. Such functions may be, for example, the receiving of ultrasound data that may or may not be pre-processed; scan conversion of received ultrasound data into an ultrasound image; processing of ultrasound data in image data frames; the display of a user interface; the control of the scanner 1331; the display of an ultrasound image on the screen 1352; the processing of using the AI model, new ultrasound image to identify a bladder and to predict the view thereof, on the new ultrasound image, thereby forming an AI model output used to apply a correct number of caliper sets on the new ultrasound image; and/or the storage, application, reinforcing and/or training of AI model 1105. The screen 1352 may comprise a touch-sensitive display (e.g., touchscreen) that can detect a presence of a touch from the operator on screen 1352 and can also identify a location of the touch in screen 1352. The touch may be applied by, for example, at least one of an individual's hand, glove, stylus, or the like. As such, the touch-sensitive display may be used for example to toggle text or to provide other inputs regarding the measurements and calculated volume. The screen 1352 and/or any other user interface may also communicate audibly. The display device 1350 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory 1356 may be computer readable data 1360, which may be used by the processor 1354 in conjunction with the computer readable instructions 1358 to provide the functions of the system 1330. Computer readable data 1360 may include, for example, settings for the scanner 1331, such as presets for acquiring ultrasound data; settings for a user interface displayed on the screen 1352; and/or data for one or more AI models within the scope of the invention. Settings may also include any other data that is specific to the way that the scanner 1331 operates or that the display device 1350 operates. It can therefore be understood that the computer readable instructions and data used for controlling the system 1330 may be located either in the computer readable memory 1334 of the scanner 1331, the computer readable memory 1356 of the display device 1350, and/or both the computer readable memories 1334, 1356.

The display device 1350 may also include a communications module 1362 connected to the processor 1354 for facilitating communication with the scanner 1331. In the illustrated example, the communications module 1362 wirelessly transmits signals to and receives signals from the scanner 1331 on wireless communication link 1344. However, as noted, in some embodiments, the connection between scanner 1331 and display device 1350 may be wired.

Referring to FIG. 14, a system 1400 is shown in which there are multiple similar or different scanners 1401, 1402, 1404 connected to their corresponding display devices 1350, 1406, 1408 and either connected directly, or indirectly via the display devices, to a communications network 1410, such as the internet. The scanners 1331, 1402, 1404 may be connected onwards via the communications network 1410 to a server 1420. The server 1420 may include a processor 1422, which may be connected to a non-transitory computer readable memory 1424 storing computer readable instructions 1426, which, when executed by the processor 1422, cause the server 1420 to provide one or more of the functions of the system 1400. Such functions may be, for example, the receiving of ultrasound frames, the processing of ultrasound data in ultrasound frames, the control of the scanners 1331, 1402, 1404, the processing of using the AI model of new ultrasound images to identify and segment boundaries of a bladder and to predict a view of the bladder, on the new ultrasound image, thereby creating an AI model output which is used to automatically apply one or more caliper sets; and/or machine learning activities related to one or more AI models 1105 (as discussed above in relation to FIGS. 1, 11 and 12).

Also stored in the computer readable memory 1424 may be computer readable data 1428, which may be used by the processor 1422 in conjunction with the computer readable instructions 1426 to provide the functions of the system 1400. Computer readable data 1428 may include, for example, settings for the scanners 1331, 1402, 1404 such as preset parameters for acquiring ultrasound data, settings for user interfaces displayed on the display devices 1350, 1406, 1408, and data for one or more AI models 1105. Settings may also include any other data that is specific to the way that the scanners 1331, 1402, 1404 operate or that the display devices 1350, 1406, 1408 operate.

It can therefore be understood that the computer readable instructions and data used for controlling the system 1400 may be located either in the computer readable memory of the scanners 1331, 1402, 1404, the computer readable memory of the display devices 1350, 1406, 1408, the computer readable memory 1424 of the server 1420, or any combination of the foregoing locations.

As noted above, even though the scanners 1331, 1402, 1404 may be different, each ultrasound frame acquired may be used by the AI model 1105 for training purposes. Likewise, ultrasound frames acquired by the individual scanners 1331, 1402, 1404 may all be processed against the AI model 1105 for reinforcement of the AI model 1105. In some embodiments, the AI models 1105 present in the display devices 1350, 1406, 1408 may be updated from time to time from an AI model 1105 present in the server 1420, where the AI model present in the server is continually trained using ultrasound frames of additional data acquired by multiple scanners 1331, 1402, 1404.

Figure 16:
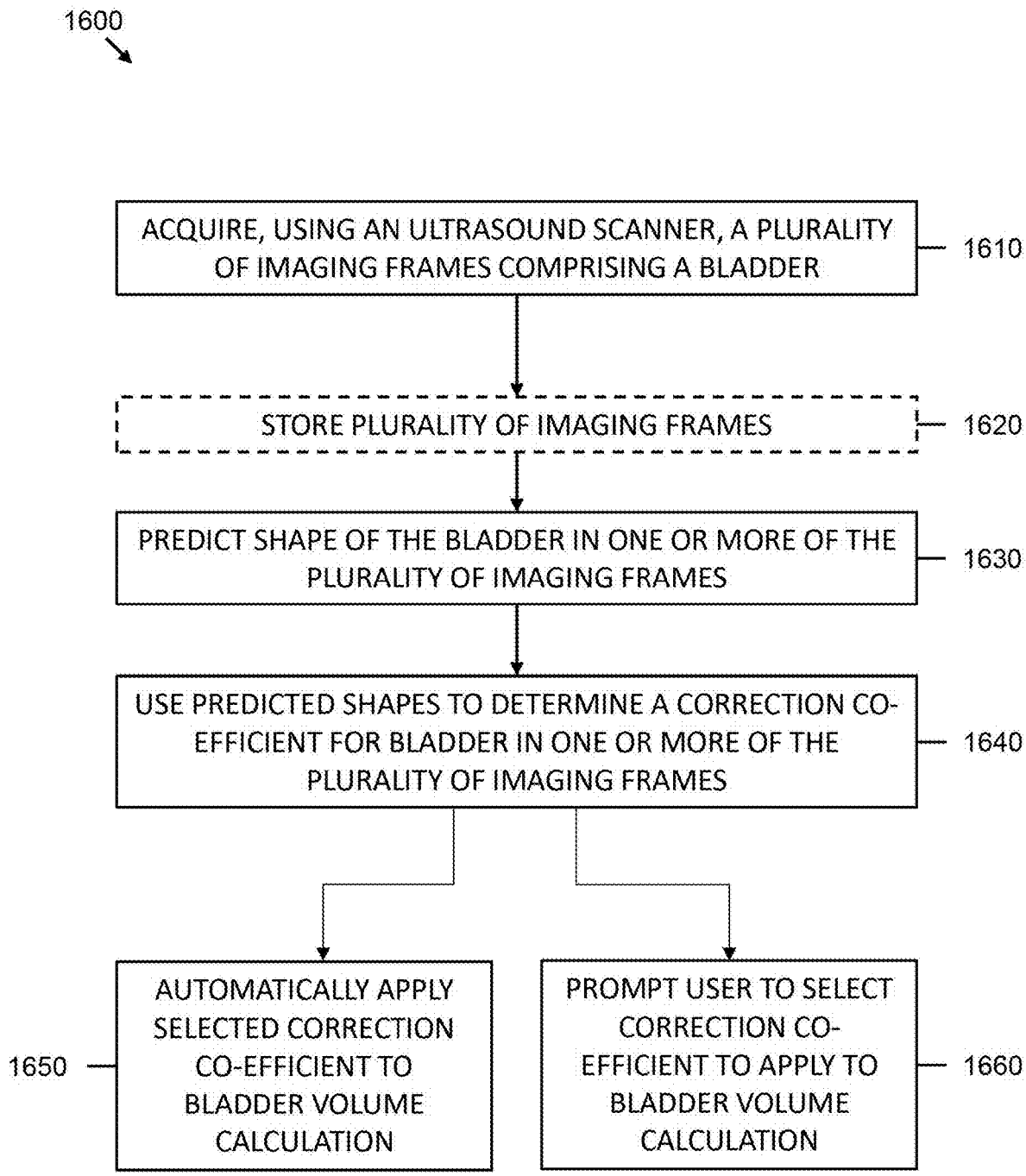
FIG. 16 is a is a flowchart diagram showing steps of a method of predicting a shape of a bladder in an ultrasound image frame acquired by an ultrasound scanner, in accordance with at least one embodiment of the present invention.
Figure 17:
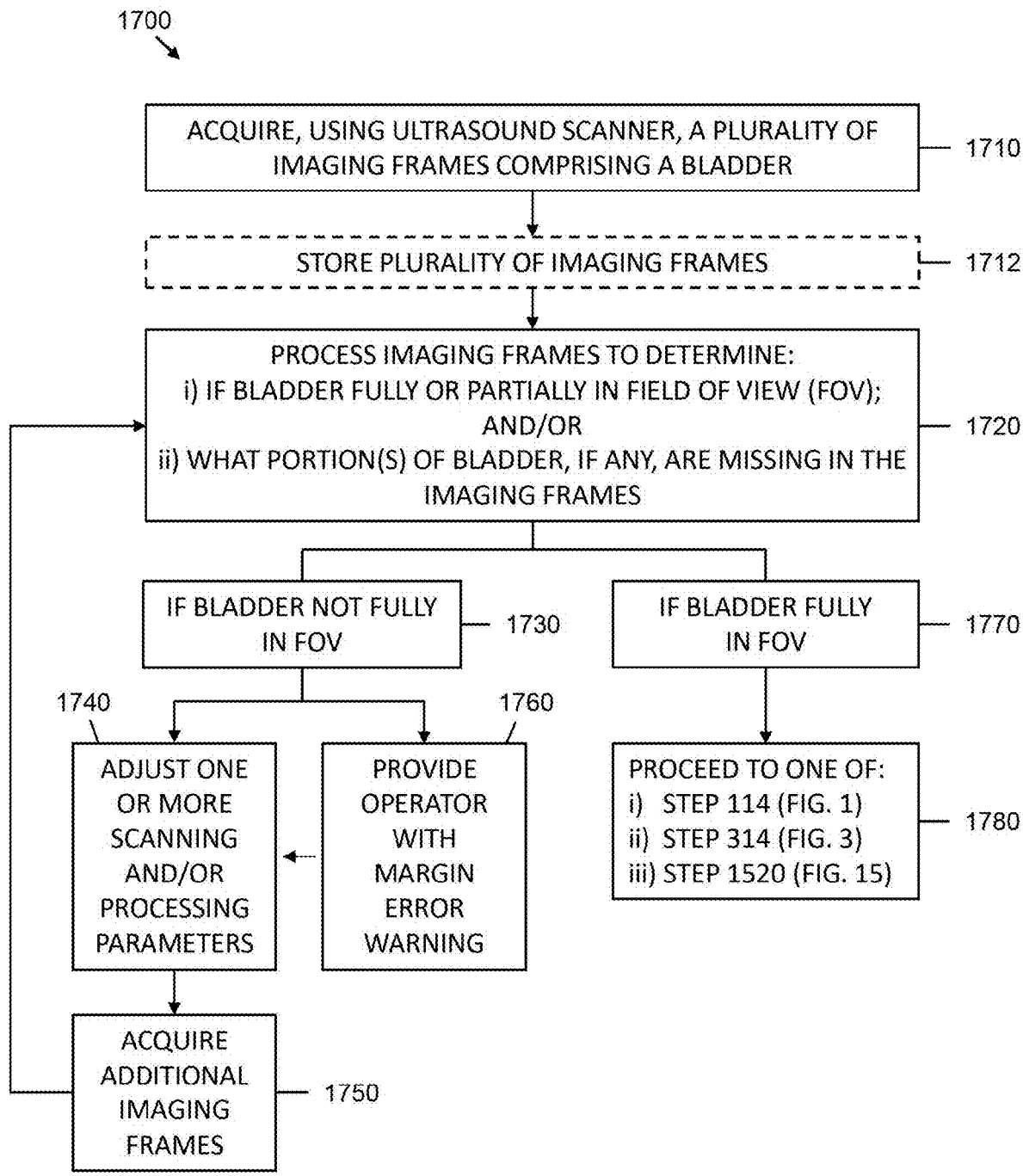
FIG. 17 is a is a flowchart diagram showing steps of a method of processing ultrasound image frames to determine the degree of completeness of an entire bladder, in a field of view, in accordance with at least one embodiment of the present invention.

Additional embodiments of the present invention are described with reference to FIGS. 15-17. In some aspects of the present invention, as described above, an ultrasound image frame is selected by a user/operator and frozen prior to the deployment of the AI model (predicting a view of a bladder in an ultrasound image frame) and subsequent use of the AI output to place a correct number of calipers sets over cross-section(s) of the bladder within each view, so as to automatically acquire those measurements and calculate bladder volume. Both views of a bladder are acquired, selected and respective images frozen and then processed through this workflow in order to complete the computation of volume. In an alternative embodiment of the invention, selection and freezing of ultrasound image frames is not required to process. Instead, a user/operator may freehand scan (for example continuously scan) a bladder/bladder region and as a plurality of ultrasound image frames are acquired and stored, an AI model is deployed to execute on a computing device communicably connected to the ultrasound scanner, wherein the AI model is trained so that when the AI model is deployed, the computing device identifies and predicts views of the bladder in the plurality of stored ultrasound image frames (for each ultrasound image frame, providing a prediction of a sagittal view or a transverse view); automatically measures cross-sections of the bladder based on the view predicted by the AI model; wherein if ultrasound image frames of both sagittal view or transverse view are acquired and each respective cross-section measured therefrom, automatically calculates bladder volume. This level of automation means that a user simply has to freehand scan or sweep the bladder area and all of the required metrics for volume calculations are collected, stored and processed, enabling conveyance of the metrics to a user. In some embodiments, as a user sweeps a probe across a bladder region of the abdomen, a bladder volume indicator and optionally a maximum bladder volume is continually displayed on a screen to provide instant or near instant feedback. By tracking images acquired during the scan in a storage/memory, the largest cross section (of the plurality of cross-sections measured in the plurality of ultrasound image frames) may be employed to calculate the maximum volume while still providing a dynamic real-time display of bladder volume.

Figure 15:
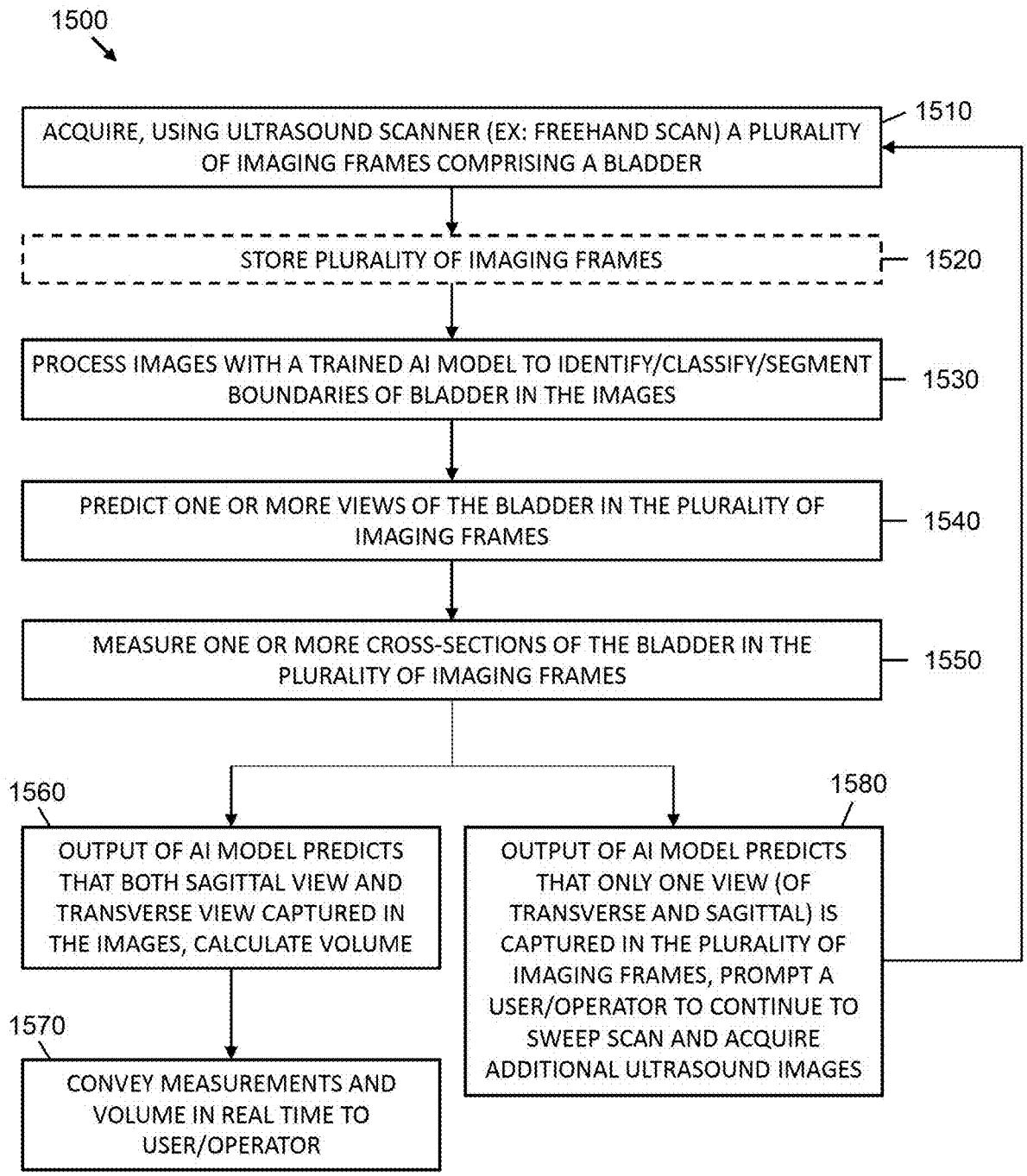
FIG. 15 is a flowchart diagram showing steps of a method of automatically applying an AI model to predict a view of a bladder, on a plurality of ultrasound image frames acquired by an ultrasound scanner, and the automatic calculation of cross-sectional measurements, on ultrasound image frames, during continuous or near continuous real time scanning, in accordance with at least one embodiment of the present invention.

Referring to FIG. 15, there is shown a flowchart diagram of a method, generally indicated at 1500, of acquisition at step 1510 of a plurality of image frames comprising a bladder (generally by a user sweeping a region over a bladder with a scanner) and, in one embodiment, storing such images at step 1520. Such image acquisition may be in real time. Such storage, in some applications of the AI model/measurement module of the present invention, is optional. While images are being stored and processed, a user may continue to acquire new ultrasound images which will, in turn be stored and processed. At step 1530, a trained AI model is deployed to execute on a computing device communicably connected to the ultrasound scanner, wherein the AI model is trained so that when the AI model is deployed, the computing device identifies and predicts, at step 1540, for each of the ultrasound imaging frames, a view of the bladder, from one of a sagittal view and a transverse view, which enables automatic placement of correct caliper sets and bladder cross-sectional measurement collection and storage at step 1550. When the AI model output predicts at step 1560 that both at least one adequate sagittal view of the bladder and at least one adequate transverse view of the bladder is captured, bladder volume is automatically calculated, and measurements conveyed to user at step 1570 in real time (optionally with the conveyance of continual updates during scanning sweeps). This conveyance may be, as described herein, through visual indicators on a display screen or via audio signals. When the AI model output predicts at step 1580 that both one or both or a sagittal view of the bladder and a transverse view of the bladder have not adequately been captured, a prompt may be conveyed to a user/operator to continue to scan and acquire ultrasound image frames, such frames being processed starting at step 1510. A bladder volume indicator (optionally with a display of measurements: length, width, and height) may be continually updated and conveyed to a user as additional images are processed during sweep scanning.

As described above with reference to Table 1 and FIG. 9, determining bladder shape, in order to select a most appropriate correction coefficient, is important in accurate bladder volume assessments. Correction coefficients are shape dependent. In a further embodiment and with reference to FIG. 16, there is provided, generally at 1600, a method for automatically determining a correction coefficient for calculating bladder volume, which comprises acquiring from an ultrasound scanner a plurality of ultrasound image frames comprising a bladder at step 1610 (such acquisition may be in real time), optionally storing such ultrasound images at step 1620, predicting a shape of the bladder in one or more of the plurality of ultrasound image frames at 1630, and employing the predicted shape to determine a more suitable correction coefficient at step 1640. This correction coefficient may be automatically applied to bladder volume calculations using a measurement workflow at 1650 or a user may be prompted to select and confirm the predicted bladder shape and correction coefficient at steps 1660, prior to calculation. It is to be understood that predicting, at step 1630, may be enabled by i) the deployment of a shape-trained AI model against which the plurality of ultrasound image frames are processed; and/or ii) the use of post-processing/image processing techniques, which provide statistical probabilities that one or more bladder shapes identified in the ultrasound images are one or more of the shapes set out in FIG. 9. In either of these ways, a shape of a bladder identified in the plurality of ultrasound image frames may be matched most closely with one of the shapes of FIG. 9 so as to most accurately apply a correction coefficient to the bladder volume calculation formula. This determination method may result in a change in correction coefficient, for example, a change from a default correction coefficient.

Depending on the probe being used to acquire ultrasound images, the field of view of the image may not capture the entirety of a bladder. A number of other factors may also impact field of view, for example, in using a phased array probe, which has a narrower field of view, the top left and top right corners of the bladder may be cut off from the ultrasound image. In another aspect of the present disclosure, there is provided generally at 1700 in FIG. 17, a method for increasing the accuracy of automatic acquisition of cross-sectional measurements of a bladder, in a field of view (FOV) in an ultrasound image, which comprises, at step 1710, acquiring from an ultrasound scanner a plurality of ultrasound image frames comprising a bladder, optionally storing the plurality of ultrasound images at step 1712, processing the plurality of ultrasound image frames at step 1720 to determine if a bladder is fully/partially shown (and to what degree) in each FOV and what portions of the bladder, if any, are missing in each FOV. If a bladder is only partially shown in FOV or not shown in FOV, at step 1730, adjustments may be made to one or more scanning and/or processing parameters to increase visibility of cross-sectional measurements in a FOV, in additional imaging frames. In addition, or alternatively at step 1760, a user/operator may be provided with a margin of error warning pertaining to volume any calculation derived from such ultrasound images. After any adjustments at step 1740 (such as, for example, adjustments to scanning parameters and/or processing parameters), further images may be acquired at step 1750, with a goal of having bladder fully or substantially fully within FOV or at least sufficient view of the bladder, in each orientation, for the placement of calipers and acquisition of cross-sectional measurements. If a bladder is shown in the FOV at steps 1770 (all or substantially all, or at least sufficient view of the bladder, in each orientation, for the placement of calipers and acquisition of cross-sectional measurements), then one or more of the following steps of the present invention may be pursued: step 114 (FIG. 1); steps 314 (FIG. 3) and step 1520 (FIG. 15). It is to be understood that processing, at step 1720, may be enabled by i) the deployment of a shape-trained AI model against which the plurality of ultrasound image frames are processed; and/or ii) the use of post-processing/image processing techniques, which provide statistical probabilities that one or more bladder shapes identified in the ultrasound images are one or more of the shapes set out in FIG. 9. In deploying a trained AI model for this purpose, such a model would know the shapes of bladders (see FIG. 16 also) and could readily detect if part of the bladder (of that known shape) is cut off from the ultrasound image frame (for example if the bladder is a discontinuous shape). At step 1740, the goal of automatically changing one or more imaging parameters (for example, beam steer at higher angles to the left and right) to try to capture portions of the bladder that are not in the field of view. Additionally, or alternatively, at step 1740, a user may be prompted to move the probe to get a better (fuller) view of the bladder.

There are a variety of uses of the AI model/measurement tool of the present invention and the present application is not intended to be limited as to application and uses. In one aspect, the AI model/measurement tool, which offers a non-invasive means to seamlessly and accurately measure bladder volume within seconds, enhances workflows for clinicians in both acute care and outpatient settings and prevents unnecessary catheterization (thereby reducing complications) for patients in urinary retention. This not only reduces complications and length of in-patient stay but also replaces the need for bladder scanners, making it a significant advancement from an enterprise perspective. Without limitation, target clinical specialties include emergency medicine, critical care, nursing (hospital/outpatient), and urology.

An exemplary application of the AI model/measurement tool of the present invention is in area of pelvic floor/bladder base elevation assessment. More specifically, one indirect means of assessing health of a pelvic floor is a via measurement of the amount of pelvic floor elevation during pelvic and abdominal muscle contraction with a diagnostic ultrasonic imaging device, wherein a proxy for this elevation is depth of a bladder, above the pelvic floor. In one aspect, a subject consumes fluid prior to testing (to fill or substantially fill a bladder of the subject) and are then an ultrasound probe is positioned on the subject for the acquisition of a plurality of ultrasound images. The trained AI model as described herein is deployed on one or more acquired image frames so as to predict, identify and confirm a transverse view/plane (preferably this is achieved by an operator scanning suprapubically angled in a caudal/posterior direction to obtain a clear image of the inferoposterior aspect of the bladder). If and when an AI model output predicts a transverse view, a measurement module, receiving such an output, automatically applies a caliper set to measure bladder depth while a subject then performs one or more maximum contractions and maintains at least one contraction during image acquisition. A depth measurement, so determined, represents an amount of bladder base displacement from the resting position at the end of each contraction. It is to be understood that the AI model/measurement tool of the present invention may be applied on one or more selected and frozen ultrasound images or may be applied on a continual series of acquired ultrasound images, for example as stored ultrasound images.

D. Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed in parallel or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

In a first broad aspect of the present disclosure, there is provided a method of for automatically measuring a bladder on an ultrasound image feed, acquired from an ultrasound scanner comprising displaying, on a screen that is communicatively connected to the ultrasound scanner, the ultrasound image feed comprising ultrasound image frames of a bladder; deploying an AI model to execute on a computing device communicably connected to the ultrasound scanner, wherein the AI model is trained so that when the AI model is deployed, the computing device identifies and predicts a view of the bladder, from one of a sagittal view and a transverse view; acquiring, at the computing device, a new ultrasound image during ultrasound scanning; processing, using the AI model, the new ultrasound image to identify and predict the view of the bladder, wherein the prediction is an AI model output; if the AI model output predicts that the new ultrasound image comprises a sagittal view of the bladder, automatically applying one caliper set along a superior-inferior dimension of the bladder and measuring the superior-inferior dimension; and if the AI model output predicts that the new ultrasound image comprises a transverse view of the bladder, applying two caliper sets along each of a length and a width of the bladder and measuring the length and width thereof.

In some embodiments, the AI model identifies and segments boundaries of the bladder in the ultrasound image frame and the AI output comprises a display on the screen of a segmented bladder. In some embodiments, a workflow application on multi-purpose electronic device, which is communicatively coupled with the ultrasound scanner, receives the AI model output and, for the sagittal view of the bladder, automatically places the one caliper set and acquires the measurement therefrom and, for the transverse view of the bladder, automatically places the two caliper sets, and acquires the measurements from either one or two caliper sets. In some embodiments, a new ultrasound image comprises a sagittal view of the bladder and a subsequent ultrasound image of the bladder is acquired in transverse view, by rotating the ultrasound scanner 90 degrees counterclockwise and an additional step comprises calculating bladder volume using the superior-inferior dimension, the length and the width. In some embodiments, a new ultrasound image comprises a transverse view of the bladder and a subsequent ultrasound image of the bladder is acquired in sagittal view, by rotating the ultrasound scanner 90 degrees clockwise and an additional step comprises calculating bladder volume using the superior-inferior dimension, the length and the width. In some embodiments, a method provides that in the transverse view, placing two measurement calipers (sets) are automatically placed orthogonal to each other. In some embodiments, a method provides that calculating the bladder volume comprises the step of multiplying the superior-inferior dimension by the length and the width and a correction co-efficient. In some embodiments, a method additionally includes a step of directing a user to rotate the ultrasound scanner after acquiring the new ultrasound image frame, to acquire a subsequent ultrasound image frame in a different view from that of the new ultrasound image frame, for processing using the AI model. In some embodiments, a method employs a screen within a multi-purpose electronic device which is communicatively coupled with the ultrasound scanner and an additional step of indicating volume of the bladder to a user of ultrasound scanner is via at least one of a visual signal on the display or an audio signal. In some embodiments, a method provides that an AI model is trained with a plurality of training ultrasound images comprising labelled segmented boundaries of bladders, in plurality of views, which are, one of: i) generated by one of a manual or semi automatic means; or ii) tagged from an identifier menu by one of a manual, semi automatic means or fully automatic means. In some embodiments, a method comprises training the AI model with one or more of the following: i) supervised learning; ii) unsupervised learning; iii) previously labelled ultrasound image datasets; and iv) cloud stored data. In some embodiments, a method additionally comprises a step of storing measurements identified by the calipers.

As such, in another aspect of the present invention, there is provided a method of determining bladder base elevation, which comprises acquiring, (preferably in real time), a plurality of ultrasound image frames comprising a bladder, optionally storing the plurality of image frames; deploying an AI model to execute on a computing device communicably connected to the ultrasound scanner, wherein the AI model is trained so that when the AI model is deployed, the computing device identifies and predicts views of the bladder in the plurality of stored ultrasound image frames (for each ultrasound image frame, providing a prediction of a sagittal view or a transverse view); for a transverse view, automatically measuring depth cross-section of the bladder based on the view predicted by the AI model. In some aspects of the invention, ultrasound image frames are acquired by freehand scanning and without a requirement for an operator to freeze image frames prior to processing with the AI model. In some aspects of the invention, an operator receives feedback (for example, visually on the display screen or via audio) during scanning indicating whether or not ultrasound image frame or frames comprise the required for purpose transverse view of the bladder and are of sufficient quality (for example, comprising full bladder in a field of view of such image or images).

In a second broad aspect of the present disclosure, there is provided a system for automatically measuring a bladder on an ultrasound image frame comprising an ultrasound scanner configured to acquire a new ultrasound image frame; a computing device communicably connected to the ultrasound scanner and configured to process the new ultrasound image frame against a trained AI model to identify and predict a view of the bladder, from one of a sagittal view and a transverse view, on the new ultrasound image frame, to form an AI model output; if the AI model output predicts that the new ultrasound image comprises a sagittal view of the bladder, automatically apply one caliper set along a superior-inferior dimension of the bladder and measure the superior-inferior dimension; if the AI model output predicts that the new ultrasound image comprises a transverse view of the bladder, apply two caliper sets along each of a length and a width of the bladder and measure the length and width thereof; and a display device comprising a screen configured to display the new ultrasound image frame.

In some embodiments, with the system of the invention, an AI model identifies and segments boundaries of the bladder in the ultrasound image frame and displays on the screen a segmented bladder. In some embodiments, with the system of the invention, a workflow application on a multi-purpose electronic device, which is communicatively coupled with the ultrasound scanner, receives the AI model output and, for the sagittal view of the bladder, automatically places the one caliper set and acquires the measurement therefrom and, for the transverse view of the bladder, automatically places the two caliper sets and acquires the measurements therefrom, wherein such calipers and placement is displayed on the screen. In some embodiments, with the system of the invention, a new ultrasound image frame on the screen comprises a sagittal view of the bladder and a subsequent ultrasound image frame of the bladder is acquired and displayed on the screen in transverse view, by rotating the ultrasound scanner 90 degrees counterclockwise. and bladder volume is calculated using the superior-inferior dimension, the length and the width. In some embodiments, with the system of the invention, a new ultrasound image frame on the screen comprises a transverse view of the bladder and a subsequent ultrasound image frame of the bladder is acquired and displayed on the screen in sagittal view, by rotating the ultrasound scanner 90 degrees clockwise and bladder volume is calculated using the superior-inferior dimension, the length and the width. In some embodiments, with the system of the invention, a workflow application calculates the bladder volume by multiplying the superior-inferior dimension by the length and the width and a correction co-efficient. In some embodiments, with the system of the invention, a workflow application signals the volume of the bladder to a user of the ultrasound scanner via at least one of a visual signal on the display screen or an audio signal.

In a third broad aspect of the present disclosure, there is provided a computer-readable media storing computer-readable instructions, which, when executed by a processor cause the processor to process, using a trained AI model, the new ultrasound image to identify and predict the view of the bladder, wherein the prediction is an AI model output; if the AI model output predicts that the new ultrasound image comprises a sagittal view of the bladder, automatically apply one caliper set along a superior-inferior dimension of the bladder and measure the superior-inferior dimension; and if the AI model output predicts that the new ultrasound image comprises a transverse view of the bladder, automatically apply two caliper sets along each of a length and a width of the bladder and measure the length and width thereof.

What is claimed is:

1. A method for automatically measuring a bladder on an ultrasound image feed, acquired from an ultrasound scanner comprising:
    displaying, on a screen that is communicatively connected to the ultrasound scanner, the ultrasound image feed comprising ultrasound image frames of a bladder;
    deploying an AI model to execute on a computing device communicably connected to the ultrasound scanner, wherein the AI model is trained so that when the AI model is deployed, the computing device identifies and predicts a view of the bladder, from one of a sagittal view and a transverse view;
    acquiring, at the computing device, a new ultrasound image during ultrasound scanning;
    processing, using the AI model, the new ultrasound image to identify and predict the view of the bladder, wherein the prediction is an AI model output;
    if the AI model output predicts that the new ultrasound image comprises a sagittal view of the bladder, automatically applying one caliper set along a superior-inferior dimension of the bladder and measuring the superior-inferior dimension; and
    if the AI model output predicts that the new ultrasound image comprises a transverse view of the bladder, applying two caliper sets along each of a length and a width of the bladder and measuring the length and the width thereof.

2. The method of claim 1 wherein the AI model identifies and segments boundaries of the bladder in the ultrasound image frames and the AI model output comprises a display on the screen of a segmented bladder.

3. The method of claim 1, wherein a workflow application on a multi-purpose electronic device, which is communicatively coupled with the ultrasound scanner, receives the AI model output and, for the sagittal view of the bladder, automatically places the one caliper set and acquires the measurement therefrom and, for the transverse view of the bladder, automatically places the two caliper sets, and acquires the measurements from either one or two caliper sets.

4. The method of claim 1 wherein the new ultrasound image comprises a sagittal view of the bladder and a subsequent ultrasound image of the bladder is acquired in transverse view, by rotating the ultrasound scanner 90 degrees counterclockwise and an additional step comprises calculating bladder volume using the superior-inferior dimension, the length and the width.

5. The method of claim 1 wherein the new ultrasound image comprises a transverse view of the bladder and a subsequent ultrasound image of the bladder is acquired in sagittal view, by rotating the ultrasound scanner 90 degrees clockwise and an additional step comprises calculating bladder volume using the superior-inferior dimension, the length and the width.

6. The method of claim 1, wherein, in the transverse view, placing the two measurement calipers orthogonal to each other.

7. The method of claim 1 further comprising a step of calculating the bladder volume by multiplying the superior-inferior dimension by the length and the width and a correction co-efficient.

8. The method of claim 1 additionally including a step of directing a user to rotate the ultrasound scanner after acquiring the new ultrasound image, to acquire a subsequent ultrasound image in a different view from that of the new ultrasound image, for processing using the AI model.

9. The method of claim 1, wherein the screen is within a multi-purpose electronic device which is communicatively coupled with the ultrasound scanner and an additional step of indicating volume of the bladder to a user of ultrasound scanner is via at least one of a visual signal on the screen or an audio signal.

10. The method of claim 1 wherein the AI model is trained with a plurality of training ultrasound images comprising labelled segmented boundaries of bladders, in plurality of views, which are, one of: i) generated by one of a manual or semi automatic means; or ii) tagged from an identifier menu by one of a manual, semi automatic means or fully automatic means.

11. The method of claim 1 comprising training the AI model with one or more of the following: i) supervised learning; ii) unsupervised learning; iii) previously labelled ultrasound image datasets; and iv) cloud stored data.

12. The method of claim 1 additionally comprising a step of storing measurements identified by the calipers.

13. A system for automatically measuring a bladder on an ultrasound image frame comprising:
    an ultrasound scanner configured to acquire a new ultrasound image frame;
    a computing device communicably connected to the ultrasound scanner and configured to:
        process the new ultrasound image frame against a trained AI model to identify and predict a view of the bladder, from one of a sagittal view and a transverse view, on the new ultrasound image frame, to form an AI model output;
        if the AI model output predicts that the new ultrasound image frame comprises a sagittal view of the bladder, automatically apply one caliper set along a superior-inferior dimension of the bladder and measure the superior-inferior dimension;
        if the AI model output predicts that the new ultrasound image frame comprises a transverse view of the bladder, apply two caliper sets along each of a length and a width of the bladder and measure the length and width thereof; and
    a display device comprising a screen configured to display the new ultrasound image frame.

14. The system of claim 13 wherein the AI model is configured to identify and segment boundaries of the bladder in the ultrasound image frame and displays on the screen a segmented bladder.

15. The system of claim 13 wherein the new ultrasound image frame on the screen comprises a sagittal view of the bladder and a subsequent ultrasound image frame of the bladder is acquired and displayed on the screen in transverse view, by rotating the ultrasound scanner 90 degrees counterclockwise, and bladder volume is calculated using the superior-inferior dimension, the length and the width.

16. The system of claim 13 wherein the new ultrasound image frame on the screen comprises a transverse view of the bladder and a subsequent ultrasound image frame of the bladder is acquired and displayed on the screen in sagittal view, by rotating the ultrasound scanner 90 degrees clockwise and bladder volume is calculated using the superior-inferior dimension, the length and the width.

17. The system of claim 13 further comprising a workflow application on a multi-purpose electronic device, which is communicatively coupled with the ultrasound scanner, and which is configured to receives the AI model output and, for the sagittal view of the bladder, automatically place the one caliper set and acquire the measurement therefrom and, for the transverse view of the bladder, automatically place the two caliper sets and acquire the measurements therefrom, wherein such calipers and placement is displayed on the screen.

18. The system of claim 17 wherein the workflow application is configured to calculates the bladder volume by multiplying the superior-inferior dimension by the length and the width and a correction co-efficient.

19. The system of claim 17 wherein the workflow application is configured to signal the volume of the bladder to a user of the ultrasound scanner via at least one of a visual signal on the screen or an audio signal.

* * * * *

UNITED STATES PATENT AND TRADEMARK OFFICE
CERTIFICATE OF CORRECTION

| | |
|---|---|
| PATENT NO. | : 12,419,613 B2 |
| APPLICATION NO. | : 18/407290 |
| DATED | : September 23, 2025 |
| INVENTOR(S) | : Kris Dickie et al. |

Page 1 of 1

It is certified that error appears in the above-identified patent and that said Letters Patent is hereby corrected as shown below:

In the Claims

In Claim 17, Line 4, the word "receives" should be "receive".

In Claim 18, Line 2, the word "calculates" should be "calculate".

Signed and Sealed this
Twenty-first Day of October, 2025

John A. Squires
*Director of the United States Patent and Trademark Office*